US007097970B2

(12) United States Patent
Petropoulos et al.

(10) Patent No.: US 7,097,970 B2
(45) Date of Patent: Aug. 29, 2006

(54) METHODS OF EVALUATING VIRAL ENTRY INHIBITORS USING PATIENT DERIVED ENVELOPE PROTEIN CONSTRUCTS

(75) Inventors: Christos J. Petropoulos, Half Moon Bay, CA (US); Neil T. Parkin, Belmont, CA (US); Jeanette M. Whitcomb, San Mateo, CA (US); Wei Huang, Foster City, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 0 days.

(21) Appl. No.: 09/874,475

(22) Filed: Jun. 4, 2001

(65) Prior Publication Data

US 2002/0182592 A1 Dec. 5, 2002

(51) Int. Cl.
*C12Q 1/70* (2006.01)

(52) U.S. Cl. .............. 435/5; 435/6; 435/7.1; 435/7.21; 435/69.1; 435/320.1; 514/44; 530/23.72

(58) Field of Classification Search ............ 424/93.1, 424/93.2; 435/5, 6, 69.1, 235.1, 320.1, 325, 435/365.1, 455, 7.1, 7.21; 514/44; 536/23.72
See application file for complete search history.

(56) References Cited

U.S. PATENT DOCUMENTS

| 5,837,464 | A | | 11/1998 | Capon et al. |
| 5,939,320 | A | | 8/1999 | Littman et al. |
| 6,103,462 | A | * | 8/2000 | Paulous et al. ............... 435/5 |
| 6,242,187 | B1 | * | 6/2001 | Capon et al. ................. 435/6 |
| 6,406,911 | B1 | | 6/2002 | Dong |

FOREIGN PATENT DOCUMENTS

| WO | WO 97/27319 | 1/1997 |
| WO | WO01/81608 | 4/2001 |
| WO | PCT/US03/04373 | 7/2003 |

OTHER PUBLICATIONS

Petropoulos et al. A novel phenotypic drug susceptibility assay for human immunodeficiency virus type 1. Antimicrobial Agents and Chemotherapy (Apr. 2000), vol. 44, No. 4, pp. 920-928.*
Grovit-Ferbas et al. Potential contribution of viral envelope and host genetic factors in human immunodeficiency virus type 1-infected long-term survivor. Journal of Virology (1998) vol. 72, No. 11, pp. 8650-8658.*
Gao et al. Molecular cloning and analysis of functional envelope genes from human immunodeficiency virus type-1 sequence sutypes A through G. Journal of Virology (1996) vol. 70, No. 3, pp. 1651-1667.*
Helseth et al. Rapid Complementation assays measuring replicative potential of human immunodeficiency virus type-1 envelope glycoprotein mutants. Journal of Virology (1990), vol. 64, No. 5, pp. 2416-2420.*
Trkola et al. A cell line-based neutralization assay for primary human immunodeficiency virus type-1 isolates that use either the CCR5 or the CXCR4 coreceptor. Journal of Virology (1999) vol. 73, No. 11, pp. 8966-8974.*
Luciw P. Human immunodeficiency viruses and their replication, Chapter 60, in Fields Virology, ed. Fields et al., Lippincott Williams and Wilkens, Philadelphia (1996) p. 1927.*
Alkhatib et al., 1996, "CC CKR5: A Rantes, MIP-1alpha, MIP-1 Beta Receptor as a Fusion Cofactor for Macrophage-tropic Hiv-1," *Science*, 272:1955-58.
Allaway et al., 1993, "Synergistic Inhibition of HIV-1 Envelope-Mediated Cell Fusion by CD4-based Molecules in Combination with Antibodies to Gp120 or Gp41," *Aids Res. Hum. Retroviruses*, 9:581-87.
Baba et al., 1999, "A Small-molecule, Nonpeptide CCR5 Antagonist with Highly Potent and Selective Anti-hiv-1 Activity," *Proc. Natl. Acad. Sci. USA*, 96:5698-03.
Barnes, W.M., 1994, "PCR amplification of up to 35-kb DNA with high fidelity and high yield from lambda bacteriophage templates," Proc. Natl. Acad. Sci, USA 91, 2216-20.
Baxter et al., 1999, "A Pilot Study of the Short-term Effects of Antiretroviral Management Based on Plasma Genotypic Antiretroviral Resistance Testing (Gart) in Patients Failing Antiretroviral Therapy," *Presented at the 6th Conference on Retroviruses and Opportunistic Infections*, Chicago, Il.
Bernard and Couturier, 1992, "Cell Killing by the F Plasmid Ccdb protein Involves Poisoning of DNA topoisomerase II Complexes," J. Mol. Bio. 226:735-45.
Bernard et al., 1993, "The F Plasmid CcdB protein Induces Efficient ATP-dependent Dna Cleavage by Gyrase," J Mol. Biol. 23:534-41.
Bleul et al., 1996, "The Lymphocyte Chemoattractant Sdf-1 Is a Ligand for Lestr/fusin and Blocks Hiv-1 Entry," Nature 382:829-33.
Bridger et al., 1999, "Synthesis and Structure-activity Relationships of Phenylenebis(methylene)-linked Bis-azamacrocycles That Inhibit HIV-1 and HIV-2 Replication by Antagonism of the Chemokine Receptor CXCR4," J. Med. Chem. 42:3971-81.

(Continued)

*Primary Examiner*—Ulrike Winkler
(74) *Attorney, Agent, or Firm*—Jones Day

(57) ABSTRACT

The invention provides a method for identifying whether a compound inhibits entry of a virus into a cell which comprises: (a) obtaining nucleic acid encoding a viral envelope protein from a patient infected by the virus; (b) co-transfecting into a first cell (i) the nucleic acid of step (a), and (ii) a viral expression vector which lacks a nucleic acid encoding an envelope protein, and which comprises an indicator nucleic acid which produces a detectable signal, such that the first cell produces viral particles comprising the envelope protein encoded by the nucleic acid obtained from the patient; (c) contacting the viral particles produced in step (b) with a second cell in the presence of the compound, wherein the second cell expresses a cell surface receptor to which the virus binds; (d) measuring the amount of signal produced by the second cell in order to determine the infectivity of the viral particles; and (e) comparing the amount of signal measured in step (d) with the amount of signal produced in the absence of the compound, wherein a reduced amount of signal measured in the presence of the compound indicates that the compound inhibits entry of the virus into the second cell.

36 Claims, 13 Drawing Sheets

OTHER PUBLICATIONS

Coffin, 1995, "HIV Population Dynamics in Vivo: Implications for Genetic Variation, Pathogenesis, and Therapy," Science 267:483-489.

DHHS (Department of Health and Human Services), 2000, Henry Kaiser Family Foundation: "Guidelines for the Use of Antiretrovirals Agents in HIV-infected Adults and Adolescents."

Dorn et al., 2001, "Antagonists of the Human CCR5 Receptor as Anti-HIV-1 Agents. Part 1: Discovery and Initial Structure-Activity Relationships for 1-Amino-2-phenyl-4-(piperidin-1-yl) butanes," Bioorganic & Medicinal Chemistry Letters 11:259-64.

Finke et al., 2001, "Antagonists of the Human CCR5 Receptor as Anti-HIV-1 Agents. Part 4: Synthesis and Structure-Activity Relationships for 1-[N-(Methyl)-N-(phenylsulfonyl)amino]-2-(phenyl)-4-(4(4-(N-(alkyl)-N- (benzyloxycarbonyl)amino)piperidin-1-yl) butanes," Bioorganic & Medicinal Chemistry Letters 11:2475-79.

Gerdes et al., 1990, "The Hok Killer Gene Family in Gram-negative Bacteria," The New Biologist: 2:946-56.

Hertogs et al., 1998, "A Rapid Method for Simultaneous Detection of Phenotypic Resistance to Inhibitors of protease and Reverse Transcriptase in Recombinant Human Immunodeficiency Virus Type 1 Isolates from Patients Treated with Antiretroviral Drugs," Antimicrob. Agents Chemother. 42:269-76.

Hwang et al., 1997, "A Conditional Self-inactivating Retrovirus Vector That Uses a Tetracycline-responsive Expression System," J. Virol. 71: 7128-31.

Japour et al., 1993, "Standardized Peripheral Blood Mononuclear Cell Culture Assay for Determination of Drug Susceptibilities of Clinical Human Immunodeficiency Virus Type 1 Isolates," Antimicrob. Agents Chemother. 37:1095-01.

Judice et al., 1997, "Inhibition HIV Type 1 Infectivity by Constrained Alphahelical Peptides: Implications for the Viral Fusion Mechanism," Proc. Natl. Acad. Sci. U S A 94:13426-30.

Kilby et al., 1998, "Potent Suppression of HIV-1 Replication in Humans by T-20, a Peptide Inhibitor of Gp41-mediated Virus Entry," Nat Med. 4:1302-07.

Mascola et al., 2000, "HIV-1 Entry at the Mucosal Surface: Role of Antibodies in Protection," AIDS, 14 (suppl 3): S167-174.

Mascola et al., 2000, "Protection of Macaques Against Vaginal Transmission of a Pathogenic HIV-1/siv Chimeric Virus by Passive Infusion of Neutralizing Antibodies," Nature Med. 6:207-10.

Miyoshi et al, 1998, "Development of a Self-inactivating Lentivirus Vector.", J. Virol. 72:8150-57.

Naviaux et al., 1996, "The Pcl Vector System: Rapid production of Helper-free, High-titer, Recombinant Retroviruses," J. Virol. 70: 5701-05.

Petropoulos et al., 2000, "A Novel Phenotypic Drug Susceptibility Assay for HIV-1," Antimicrob. Agents & Chem. 44:920-28.

Piketty et al., 1999, "Efficacy of a Five-drug Combination Including Ritonavir, Saquinavir and Efavirenz in Patients Who Failed on a Conventional Triple-drug Regimen: Phenotypic Resistance to protease Inhibitors predicts Outcome of Therapy," Aids: 13:f71-f77.

Porter et al., 1998, "Cationic Liposomes Enhance the Rate of Transduction by a Recombinant Retroviral Vector in Vitro and in Vivo," J. Virol. 72:4832-40.

Reimann et al., 1995, "In Vivo Administration of CD4-specific Monoclonal Antibody: Effect on provirus Load in Rhesus Monkeys Chronically Infected with the Simian Immunodeficiency Virus of Macaques," Aids Res. Hum. Retroviruses 11:517-25.

Rimsky et al., 1998, "Determinants of Human Immunodeficiency Virus Type 1 Resistance to Gp41-derived Inhibitory Peptides," J. Virol. 72:986-93.

Rodriguez-Rosado et al., 1999, "Introduction of HIV Drug-resistance Testing in Clinical Practice.", Aids 13:1007-14.

Sarkar et al., 1990, "The "Megaprimer" Method of Site-Directed Mutagenesis," Biotechniques 8:404-07.

Sarkat et al., 1990, "Shedding Light on PCR contamination," Nature 343:27.

Schinazi et al., 1999, "Mutations in Retroviral Genes Associated with Drug Resistance," Intl. Antiviral News: 7:46-49.

Shi et al., 1997, "A Recombinant Retroviral System for Rapid In Vivo Analysis of Human Immunodeficiency Virus Type 1 Susceptibility to Reverse Transcriptase Inhibitors," Antimicrobrial Agents and Chemotherapy, 41:2781-85.

Wild et al., 1992, "A Synthetic Peptide Inhibitor of HIV Replication: Correlation Between Solution Structure and Viral Inhibition,", Proc. Natl. Acad. Sci. USA 89:10537-41.

http://hiv.web.lanl.gov/content/index Last accessed on May 1, 2003.

Zennou et al., 1998, "Loss of Viral Fitness Associated with Multiple Gag and Gag-pol processing Defects in Human Immunodeficiency Virus Type 1 Variants Selected for Resistance to Protease Inhibitors in vivo.", J. Virol: 72:3300-06.

Ziermann et al., 2000, "A Mutation in HIV-1 Protease, N88s, That Causes in Vitro Hypersensitivity to Amprenavir," J. Virol. 74:4414-19.

Auewarakul et al., (2001), "Application of HIV-1-Green Fluorescent Protein (GFP) Reporter Viruses in Neutralizing Antibody Assays," Asian Pacific Journal of Allergy and Immunology, 19:139-144.

Cho et al., (2001), "Polyvalent Envelope Glycoprotein Vaccine Elicits a Broader Neutralizing Antibody Response but is Unable to Provide Sterilizing Protection Against Heterologous Simian/Human Immunodeficiency Virus Infection in Pigtailed Macaques," Journal of Virology, 75(5): 2224-2234.

Dorsky et al., (1996), "Detection of HIV-1 Infection with a Green Fluorescent Protein Reporter System," Journal of Acquired Immune Deficiency Syndromes and Human Retrovirology, 13:308-313.

Hioe, et al., (1997), "Resting Cell Neutralization Assay for HIV-1 Primary Isolates," Methods: A Companion to Methods in Enzymol. 12:300-305.

Montefiore, et al., (2001)"Neutralizing Antibodies Associated with Viremia Control in a Subset of Individuals after Treatment of Acute Human Immunodeficiency Virus Type 1 Infection," Journal of Virology, 75(21): 10200-10207.

Rencher, et al., (1995), "Does the Key to a Successful HIV Type 1 Vaccine Lie among the Envelope Sequences of Infected Individuals?," AIDS Research and Human Retroviruses, 11(9): 1131-1133.

Zhange et al., "Primary Virus Envelope Cross-Reactivity of the Broadening Netralizing Antibody Response During Early Chronic Human Immunodeficiency Virus Type I Infection" Journal of Virology (1999), 73(6): 5225-5230.

Luciw P. "Incorporation of PR160$^{gag-pol}$ into Virions" Human Immunodeficiency Viruses and Their Replication, Chapter 60, in Fields Virology, ed. Fields et al., Lippincott Williams and Wilkens, Philadelphia (1996) p. 1927.

* cited by examiner

PHENOSENSE HIV ENTRY ASSAY

ENVELOPE EXPRESSION VECTOR: pHIVenv

HIV-1 EXPRESSION VECTOR: pHIVlucΔU3

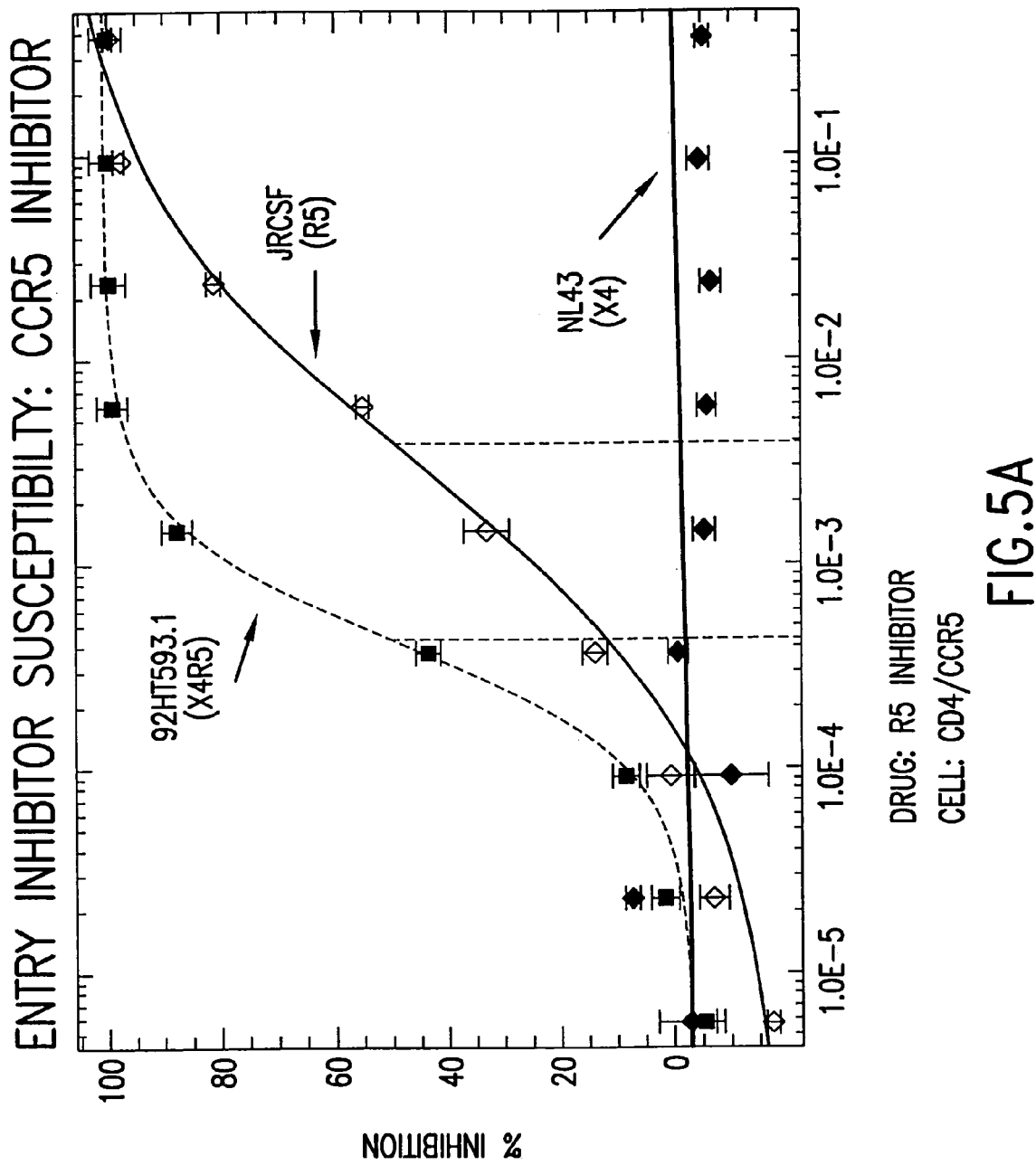

METHODS OF EVALUATING VIRAL ENTRY INHIBITORS USING PATIENT DERIVED ENVELOPE PROTEIN CONSTRUCTS

Throughout this application, various publications are referenced by author and date within the text. Full citations for these publications may be found listed alphabetically at the end of the specification immediately preceding the claims. All patents, patent applications and publications cited herein, whether supra or infra, are hereby incorporated by reference in their entirety. The disclosures of these publications in their entireties are hereby incorporated by reference into this application in order to more fully describe the state of the art as known to those skilled therein as of the date of the invention described and claimed herein.

BACKGROUND OF THE INVENTION

Virus entry is an attractive new target for anti-viral treatment, and about 10 drugs that are designed to block virus attachment or membrane fusion are currently being evaluated in preclinical or clinical studies (Richman, 1998; PhRMA, 1999; Stephenson, 1999). Enveloped animal viruses attach to and enter the host cell via the interaction of viral proteins in the virion membrane (envelope proteins) and cell surface proteins (virus receptors). Receptor recognition and binding are mediated by the surface envelope protein.

SUMMARY OF THE INVENTION

Accordingly, it is an object of the invention to provide a rapid, sensitive phenotypic assay to measure the susceptibility of a virus to inhibitors of viral entry.

A further object of the invention is to provide a retroviral vector system that produces virus particles containing viral envelope proteins derived from a variety of sources and the identification of cell lines that express viral receptors and are permissive for viral replication.

Another object of the invention is to provide an expression vector for viral envelope that is capable of accepting patient-derived segments encoding envelope genes.

Another object of the invention is to provide a bio-safe vector that represents most of the HIV-1 viral genome, but carries a luciferase reporter gene in place of the envelope region.

A further object of the invention is to the phenotypic assay which reduces the likelihood of forming recombinant infectious HIV-1, by providing a viral expression vector that carries a deletion in a transcriptional regulatory region (the 3' copy of U3) of the HIV-1 genome.

Another object of the invention is to provide an assay capable of identifying and determining receptor/co-receptor tropism, which quickly and accurately identifies patients that are infected with strains of a tropic virus.

These and other objects may be achieved by the present invention by: a method for identifying whether a compound inhibits entry of a virus into a cell which comprises: (a) obtaining nucleic acid encoding a viral envelope protein from a patient infected by the virus; (b) co-transfecting into a first cell (i) the nucleic acid of step (a), and (ii) a viral expression vector which lacks a nucleic acid encoding an envelope protein, and which comprises an indicator nucleic acid which produces a detectable signal, such that the first cell produces viral particles comprising the envelope protein encoded by the nucleic acid obtained from the patient; (c) contacting the viral particles produced in step (b) with a second cell in the presence of the compound, wherein the second cell expresses a cell surface receptor to which the virus binds; (d) measuring the amount of signal produced by the second cell in order to determine the infectivity of the viral particles; and (e) comparing the amount of signal measured in step (d) with the amount of signal produced in the absence of the compound, wherein a reduced amount of signal measured in the presence of the compound indicates that the compound inhibits entry of the virus into the second cell.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The HIV envelope expression vector (pHIUVenv) is modified to accept envelope sequences that have been amplified from patient plasma samples. The designations a/b and c/d, refer to restriction endonuclease sites positioned at the 5' and 3' end of the HIV-1 envelope polyprotein (gp160). The HIV expression vector (pHIVlucÄU3) encodes all HIV proteins except the envelope polyprotein. A portion of the envelope gene has been deleted to accommodate a indicator gene cassette, in this case, "Firefly Luciferase" that is used to monitor the ability of the virus to replicate in the presence or absence of anti-viral drugs. The 3' U3 region has been partially deleted to prevent transcription from the 5' LTR in infected cells. Virus produced in this system is limited to a single round of replication.

Figure 1A:
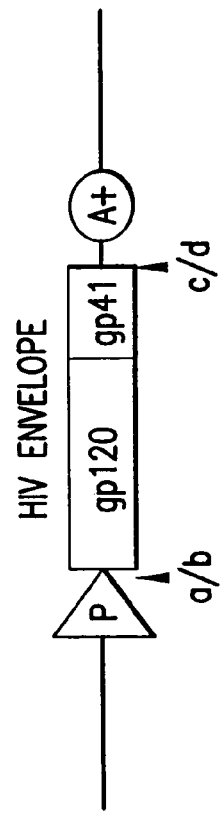
FIG. 1A. Structure of envelope expression and viral expression vectors.
Figure 1A:
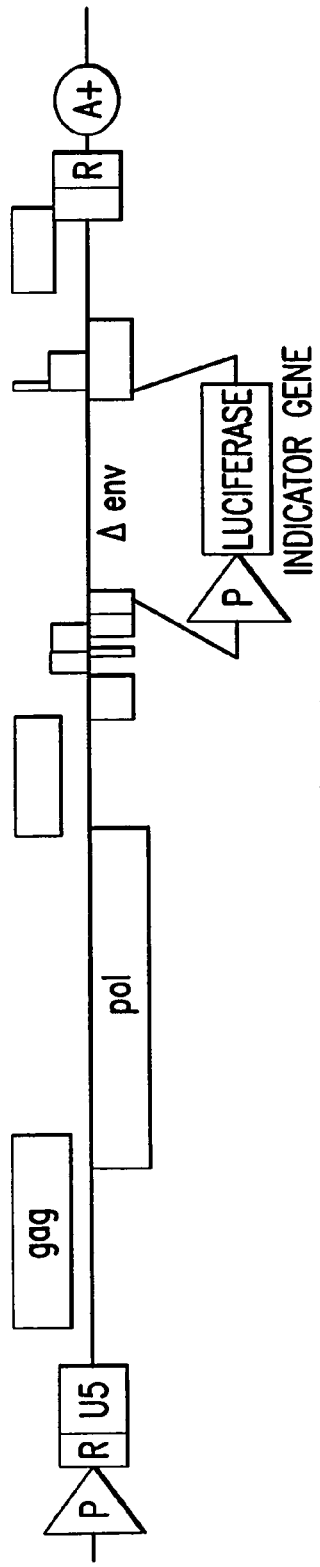
Figure 1B:
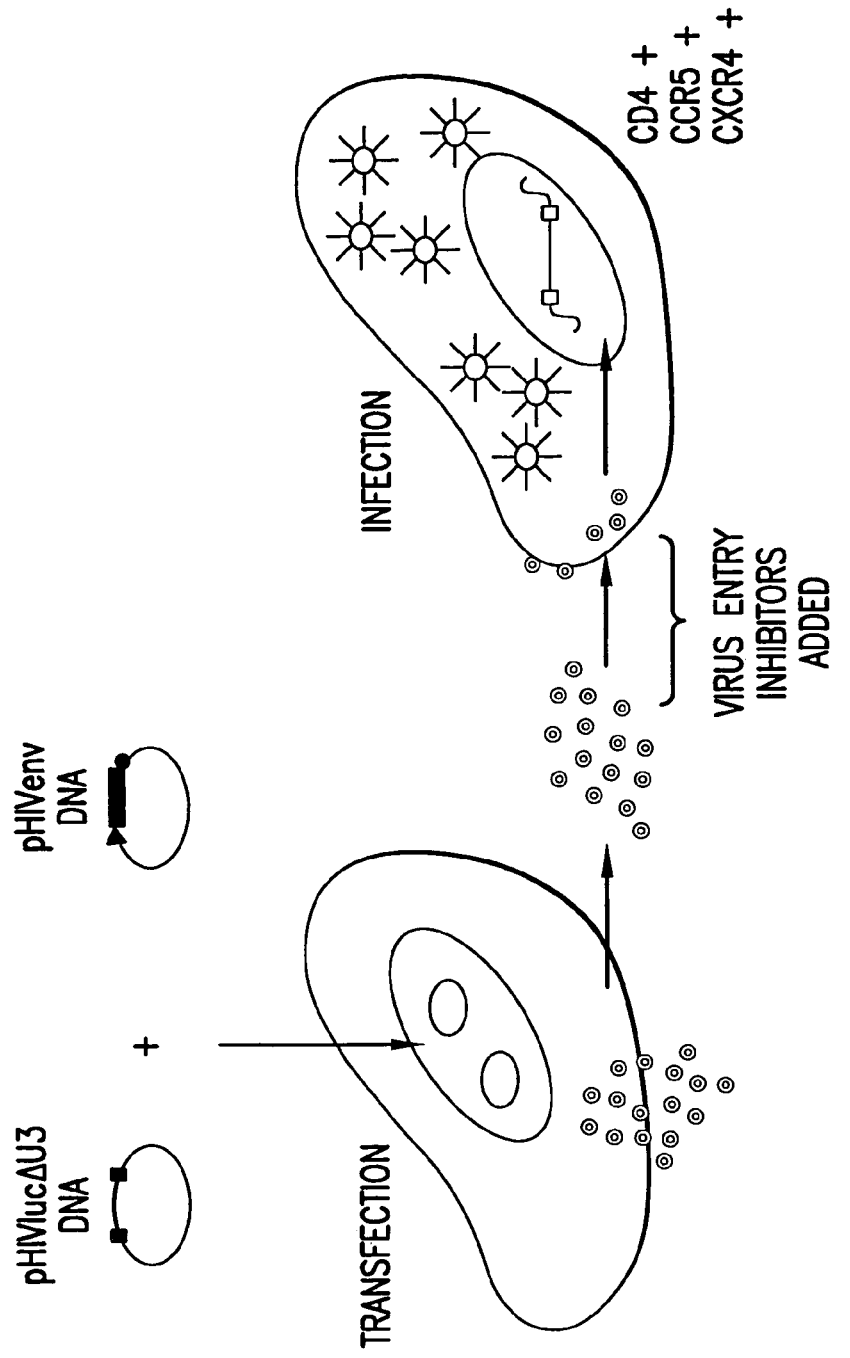

FIG. 1B. Cell Based Entry Assay

Drug susceptibility, co-receptor tropism and virus neutralization testing are performed by co-transfecting a host cell with pHIVenv and pHIVlucÄU3. The host cell produces HIV particles that are pseudo-typed with HIV envelope sequences derived from the test virus or patient sample. Virus particles are collected (~48 h) after transfection and are used to infect target cells that express HIV receptors (e.g. CD4) and co-receptors (e.g. CXCR4, CCR5). After infection (~72 h) the target cells are lysed and luciferase activity is measured. HIV must complete one round of replication to successfully infect the target host cell and produce luciferase activity. If the virus is unable to enter the target cell, luciferase activity is diminished. This system can be used to evaluate susceptibility to entry inhibitors, receptor and co-receptor tropism, and virus neutralization.

Figure 2:
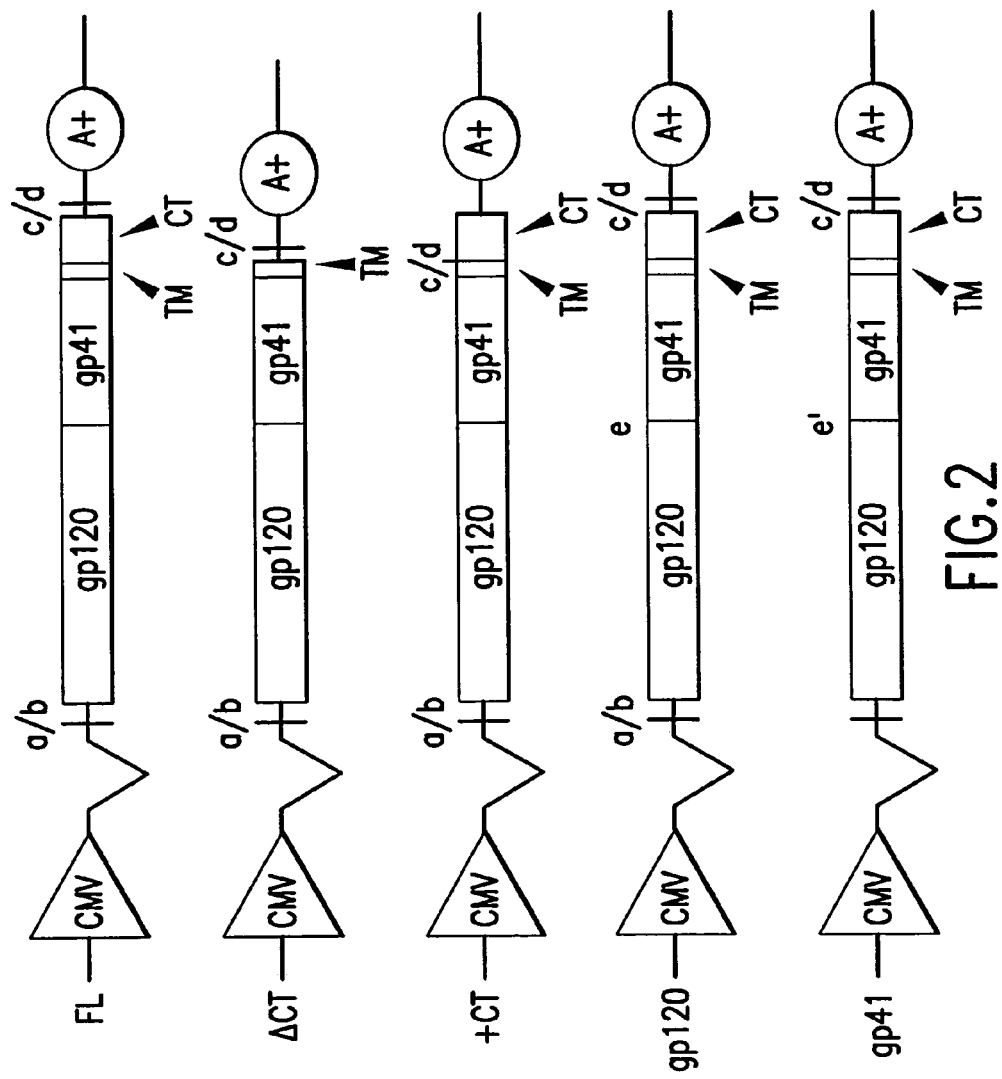

FIG. 2. HIV envelope expression vectors.

HIV envelope sequences are amplified from patient samples and inserted into expression vectors using restriction endonuclease sites (5' a/b and 3' c/d). Envelope transcription is driven by the immediate early gene promoter of human cytomegalovirus (CMV). Envelope RNA is polyadenylated using an simian virus 40 (SV40) polyadenylation signal sequence (A+). An intron located between the CMV promoter and the HIV envelope sequences is designed to increase envelope mRNA levels in transfected cells. FL—express full-length envelope proteins (gp120, gp41) ÄCT—express envelope proteins (gp120, gp21) lacking the C-terminal cytoplasmic tail domain of gp41+CT—express envelope proteins (gp120, gp41) containing a constant predefined gp41 cytoplasmic tail domain gp120—express gp120 proteins derived from the patient together with a constant pre-defined gp41. gp41—express a constant pre-defined gp120 together with gp41 proteins derived from the patient.

Figure 3A:
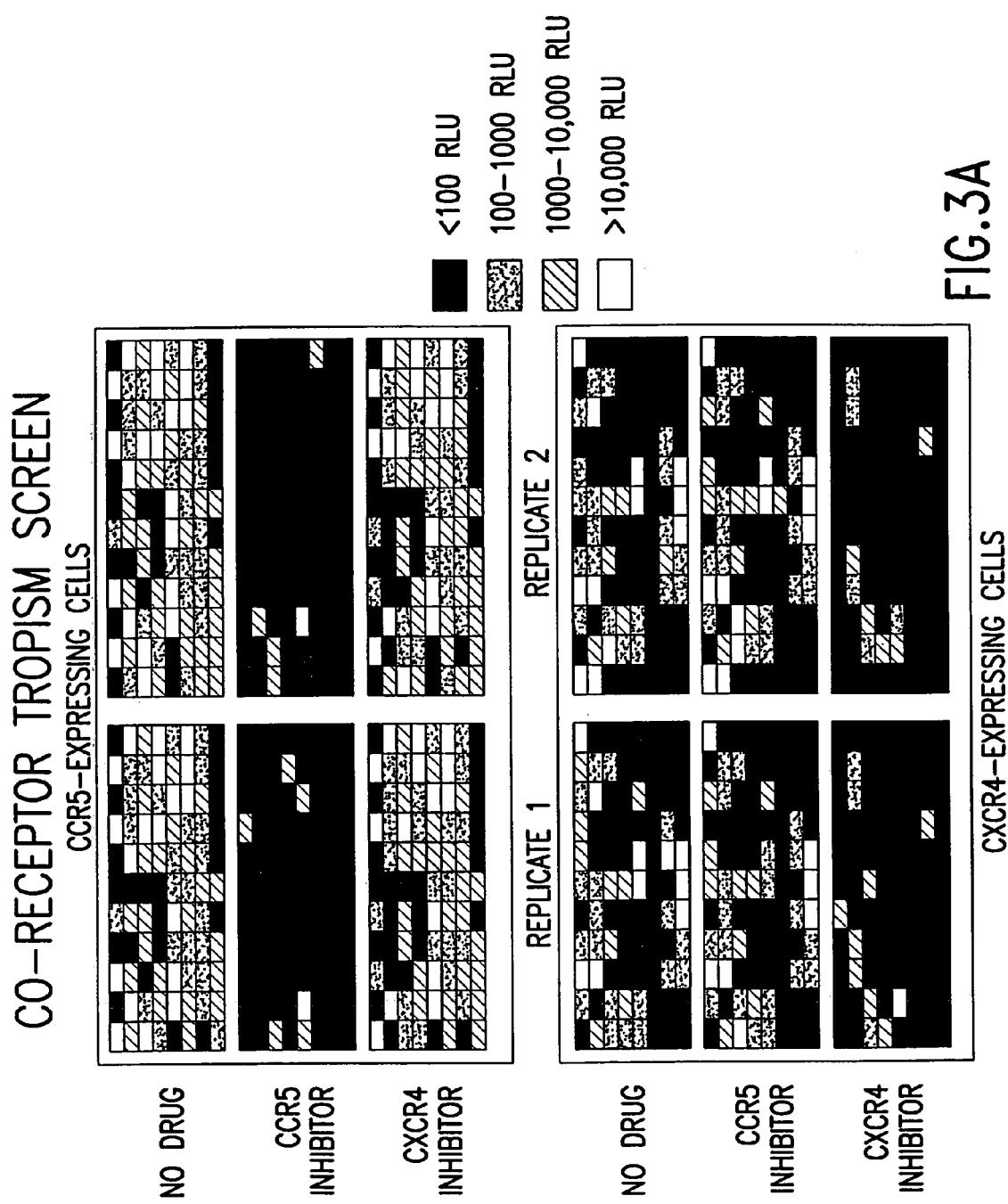

FIG. 3A. Co-receptor Tropism Screening Assay.

In this figure, the assay is performed using two cell lines. One cell line expresses CD4 and CCR5 (top six panels). The other cell line expresses CD4 and CXCR4 (bottom six panels). The assay is performed by infecting cells with a large number of recombinant virus stocks derived from cells transfected with pHIVenv and pHIVluc?U3 vectors. The example shown represents the analysis of 96 viruses formatted in a 96 well plate. Infections are performed in the absence of drug (no drug), or in the presence of a drug that preferentially inhibits either R5 tropic (CCR inhibitor) or X4 tropic (CXCR4 inhibitor) viruses. Co-receptor tropism is assessed by comparing the amount of luciferase activity produced in each cell type, both in the presence and absence of drug (see FIG. 3B for interpretation of assay results).

Figure 3B:
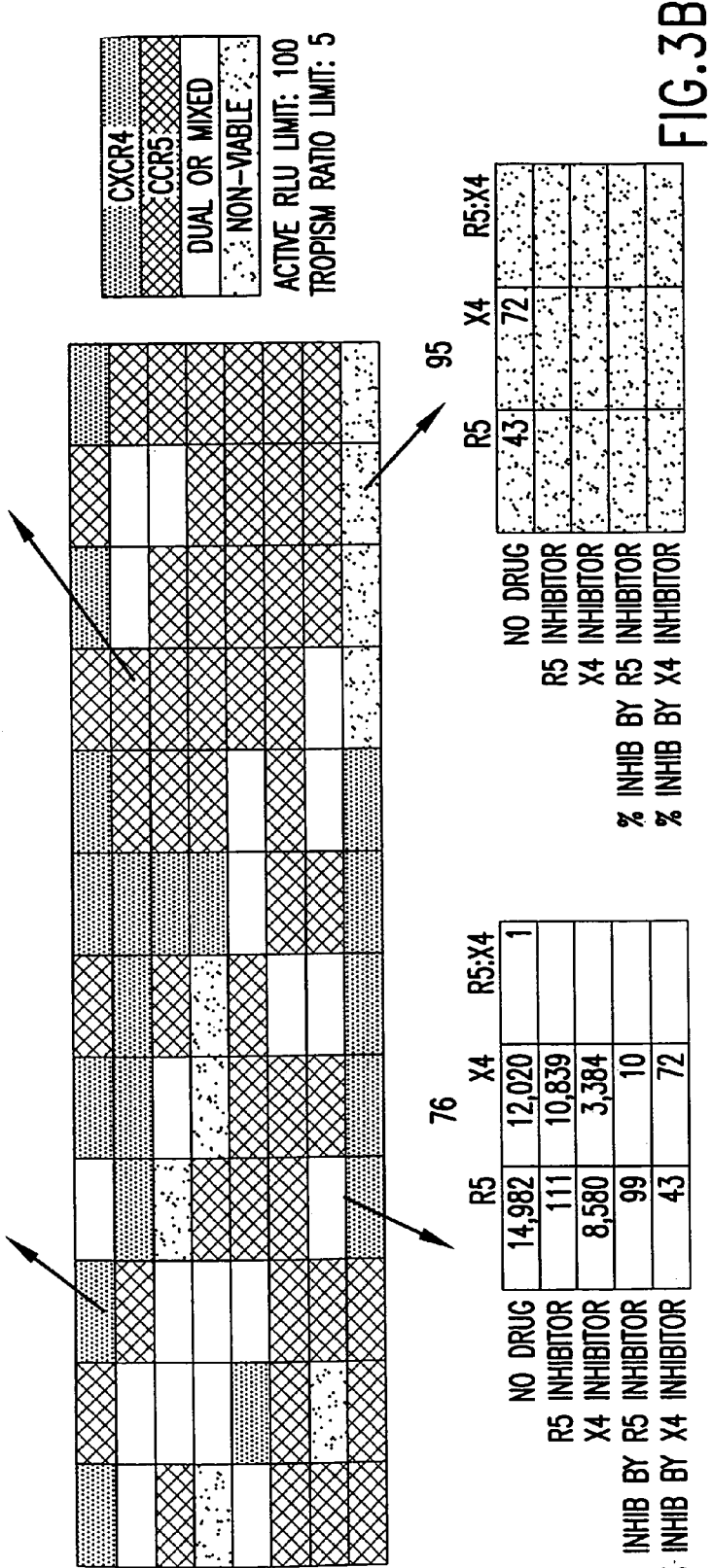

FIG. 3B. Determining co-receptor tropism.

In this figure, the results of the assay are interpreted by comparing the ability of each sample virus to infect (produce luciferase activity) in cells expressing CD4/CCR5 (R5 cells) or cells expressing CD4/CXCR4 (X4 cells). The ability of a CCR5 or CXCR4 inhibitor to specifically block infection (inhibit luciferase activity) is also evaluated. X4 tropic viruses (green panels)—infect X4 cells but not R5 cells. Infection of X4 cells is blocked by the CXCR4 inhibitor. R5 tropic viruses (blue panels)—infect R5 cells but not X4 cells. Infection of R5 cells is blocked by the CCR5 inhibitor. Dual tropic or X4/R5 mixtures (yellow panels)—infect X4 and R5 cells. Infection of R5 cells is blocked by the CCR5 inhibitor and infection of X4 cells is blocked by the CXCR4 inhibitor. Non-viable viruses (red panels)—do not replicate in either X4 or R5 cells.

Figure 4A:
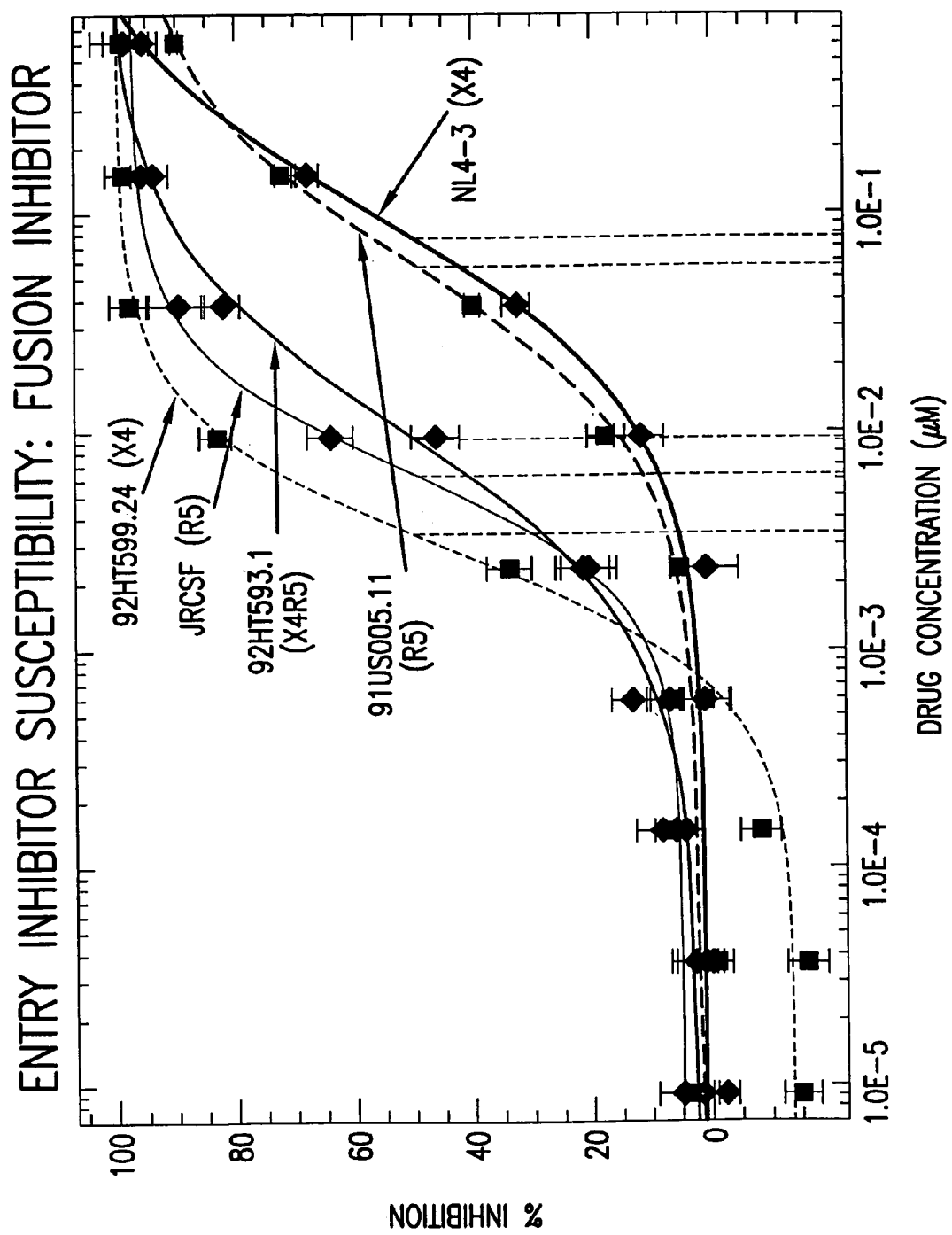

FIG. 4A. Measuring Entry Inhibitor Susceptibility: Fusion Inhibitor.

In this figure, susceptibility to the fusion inhibitor T-20 is demonstrated. Cells expressing CD4, CCR5 and CXCR4 were infected in the absence of T-20 and over a wide range of T-20 concentrations (x-axis log 10 scale). The percent inhibition of viral replication (y-axis) was determined by comparing the amount of luciferase produced in infected cells in the presence of T-20 to the amount of luciferase produced in the absence of T-20. R5 tropic, X4 tropic and dual tropic viruses were tested. Drug susceptibility is quantified by determining the concentration of T-20 required to inhibit 50% of viral replication (IC50, shown as vertical dashed lines). Viruses with lower IC50 values are more susceptible to T-20than viruses with higher IC50 values. NL4-3: well-characterized X4 tropic strain JRCSF: well-characterized R5 tropic strain 91US005.11: R5 tropic isolate obtained from the NIH AIDS Research and Reference Reagent Program (ARRRP) 92HT593.1: Dual tropic (X4R5) isolate obtained from the NIH ARRRP.92HT599.24: X4 tropic isolate obtained from the NIH ARRRP.

Figure 4B:
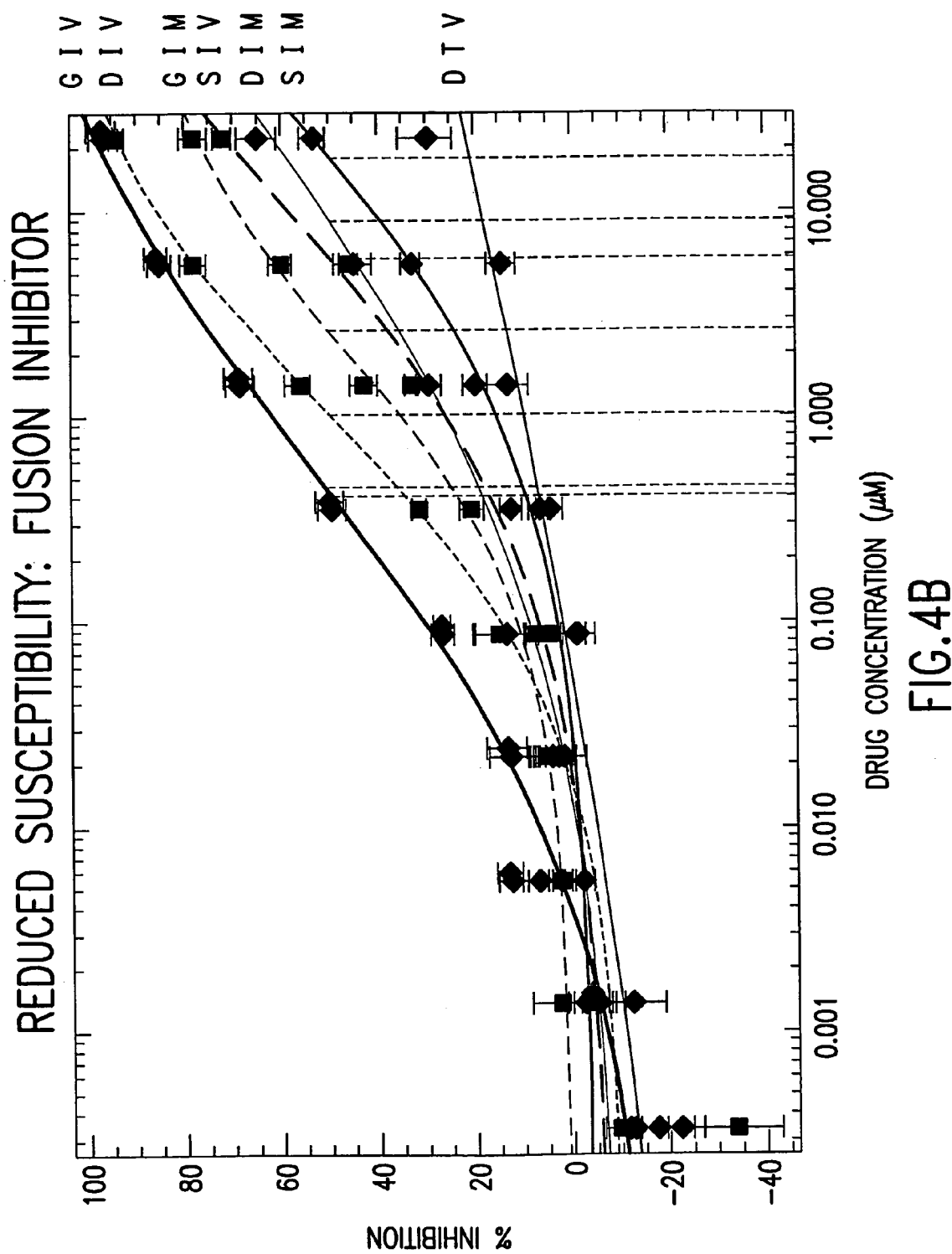
Figure 5B:
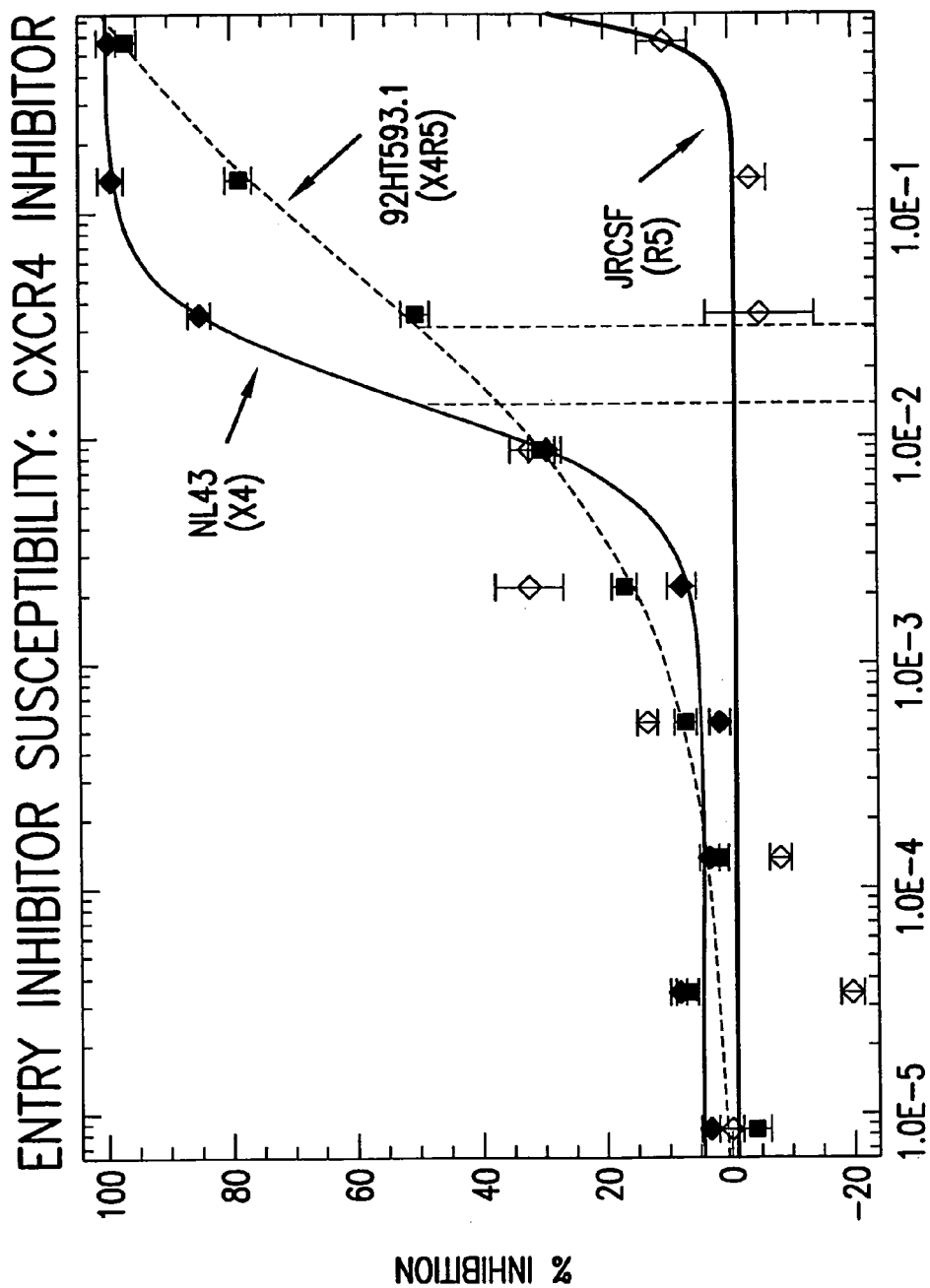

FIG. 4B. Measuring Entry Inhibitor Susceptibility: Drug Resistance Mutations.

In this figure, reduced susceptibility to the fusion inhibitor T-20 conferred by specific drug resistance mutations in the gp41 envelope protein is demonstrated. Cells expressing CD4, CCR5 and CXCR4 were infected in the absence of T-20 and over a wide range of T-20 concentrations (x-axis log 10 scale). The percent inhibition of viral replication (y-axis) was determined by comparing the amount of luciferase produced in infected cells in the presence of T-20 to the amount of luciferase produced in the absence of T-20. Isogenic viruses containing one or two specific mutations in the gp41 transmembrane envelope protein were tested (highlighted in red in the figure legend). Drug susceptibility is quantified by determining the concentration of T-20 required to inhibit 50% of viral replication (IC50, shown as vertical dashed lines). Viruses with lower IC50 values are more susceptible to T-20 than viruses with higher IC50 values.

No mutation (wildtype sequence): GIV

Single mutations: GIV, DIM, SIV

Double mutations: DIM, SIM, DTV

FIG. 5A.

Measuring Entry Inhibitor Susceptibility: CCR5 Inhibitor

In this figure, susceptibility to a CCR5 inhibitor (merck compound) is demonstrated. Cells expressing CD4 and CCR5(R5 cells) were infected in the absence of the CCR5 inhibitor and over a wide range of CCR5 inhibitor concentrations (x-axis log 10 scale). The percent inhibition of viral replication (y-axis) was determined by comparing the amount of luciferase produced in infected cells in the presence of CCR5 inhibitor to the amount of luciferase produced in the absence of CCR5 inhibitor. R5 tropic, X4 tropic and dual tropic viruses were tested. Drug susceptibility is quantified by determining the concentration of CCR5 inhibitor required to inhibit 50% of viral replication (IC50, shown as vertical dashed lines). Viruses with lower IC50 values are more susceptible to the CCR5 inhibitor than viruses with higher IC50 values. The X4 tropic virus did not infect the R5 cells. NL4-3: well-characterized X4 tropic strain JRCSF: well-characterized R5 tropic strain 92HT593.1: Dual tropic (X4R5) isolate obtained from the NIH ARRRP.

FIG. 5B.

Measuring Entry Inhibitor Susceptibility: CXCR4 Inhibitor.

In this figure, susceptibility to a CXCR4 inhibitor (AMD3100) is demonstrated. Cells expressing CD4 and CXCR4 (X4 cells) were infected in the absence of the CXCR4 inhibitor and over a wide range of CXCR4 inhibitor concentrations (x-axis log 10 scale). The percent inhibition of viral replication (y-axis) was determined by comparing the amount of luciferase produced in infected cells in the presence of CXCR4 inhibitor to the amount of luciferase produced in the absence of CXCR4 inhibitor. R5 tropic, X4 tropic and dual tropic viruses were tested. Drug susceptibility is quantified by determining the concentration of CXCR4 inhibitor required to inhibit 50% of viral replication (IC50, shown as vertical dashed lines) Viruses with lower IC50 values are more susceptible to the CCR5 inhibitor than viruses with higher IC50 values. The R5 tropic virus did not infect the X4 cells. NL4-3: well-characterized X4 tropic strain JRCSF: well-characterized R5 tropic strain 92HT593.1: Dual tropic (X4R5) isolate obtained from the NIH ARRRP.

Figure 6:
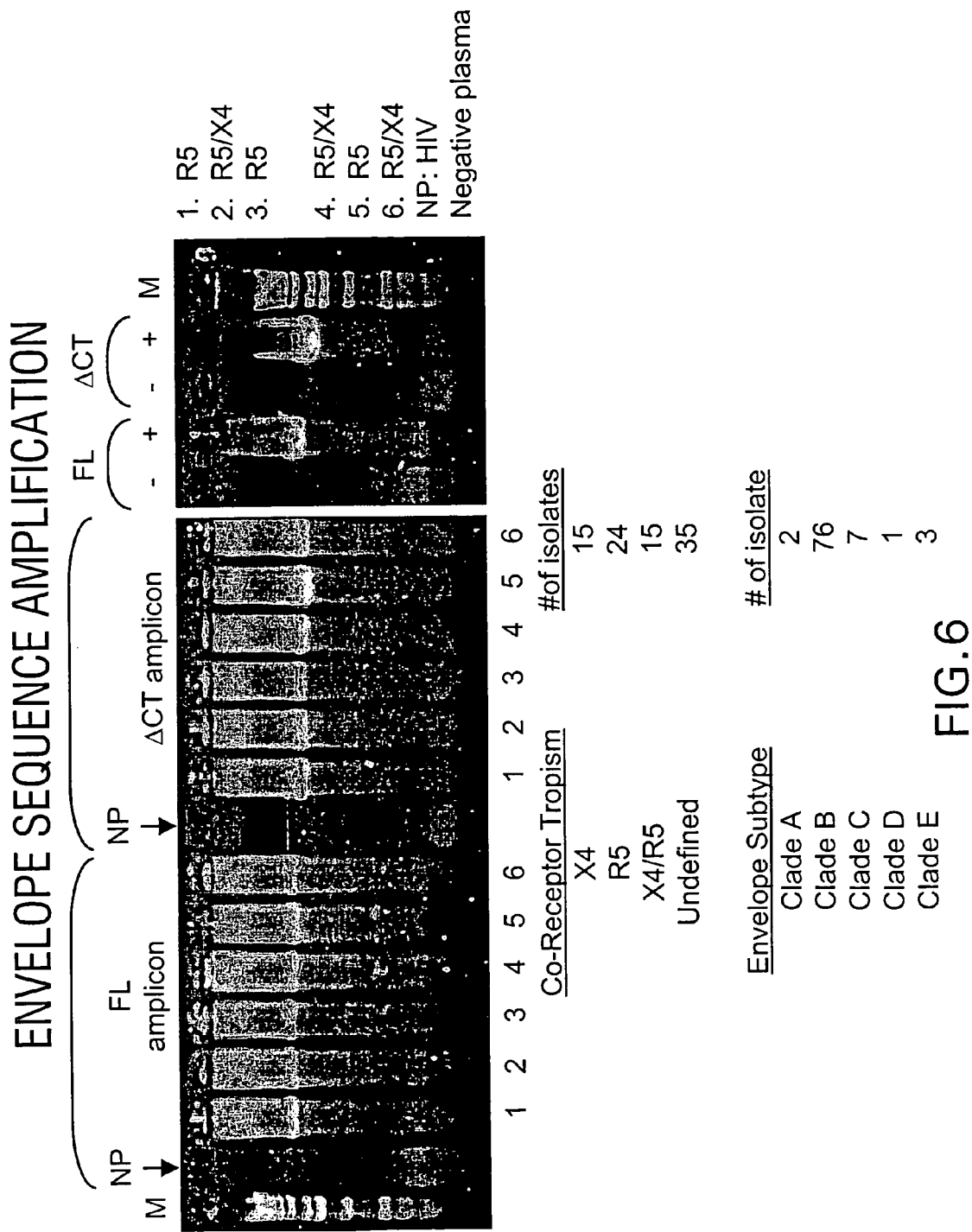

FIG. 6. Entry Inhibitor Susceptibility: Fusion Inhibitor This figure demonstrates that the amplicons corresponding to the full length envelope sequence or cytoplasmic-tail deleted envelope sequence are generated. The lane numbers correspond to the co-receptor tropism shown next to each number on the right of the gels.

Figure 7:
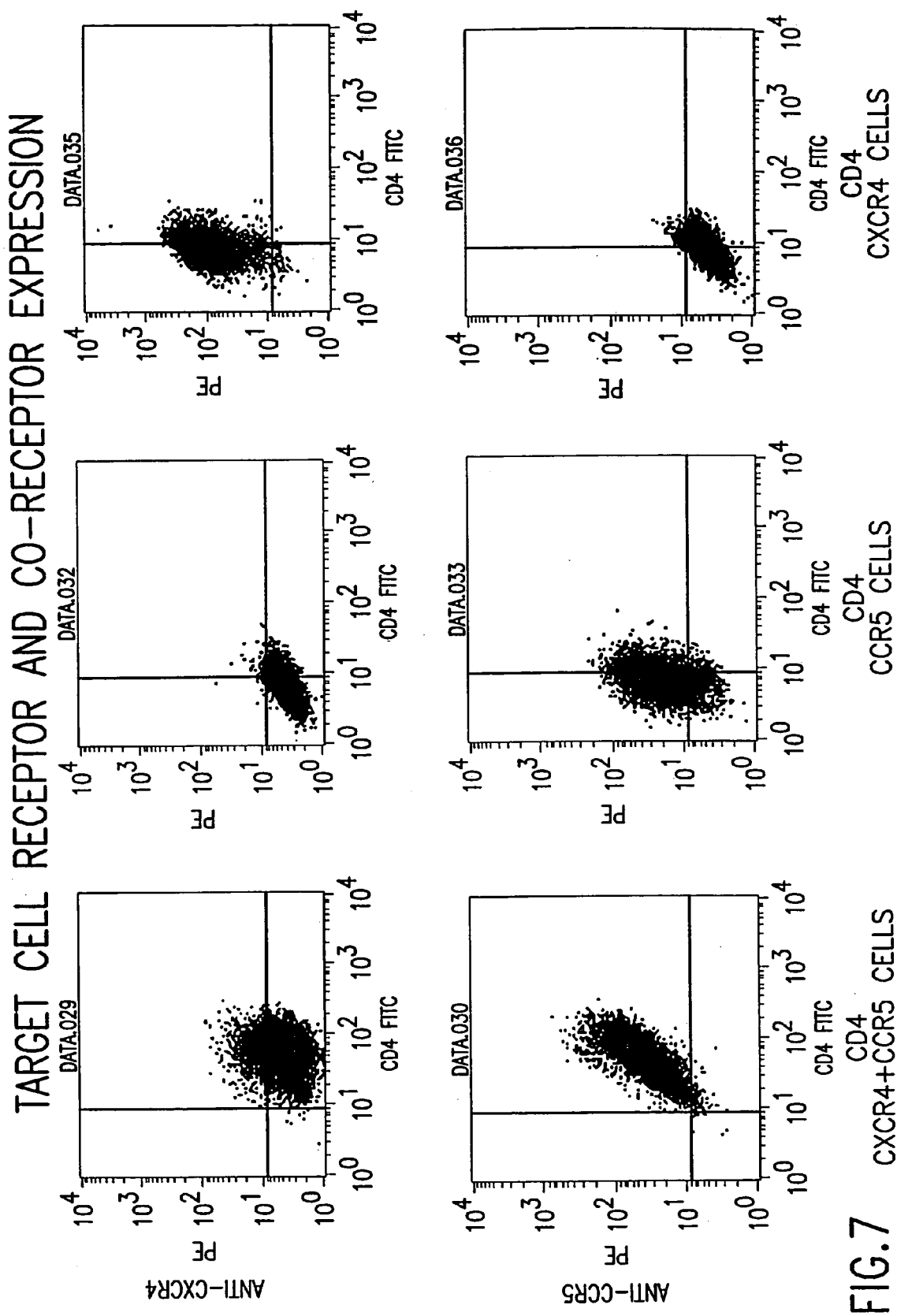

FIG. 7. Reduced Susceptibility: Fusion Inhibitor Scatter plots are shown which indicate the results from FACS (fluorescence activated cell sorting) assays using antibodies against either CCR5 or CXCR4 (shown on Y axis). The cell lines express the co-receptors listed below the plots and the CD4 fluorescence is shown along the X-axis. The anti-CXCR4 antibody binds most strongly with the cells which express the corresponding co-receptor, CXCR-4.

Figure 8:
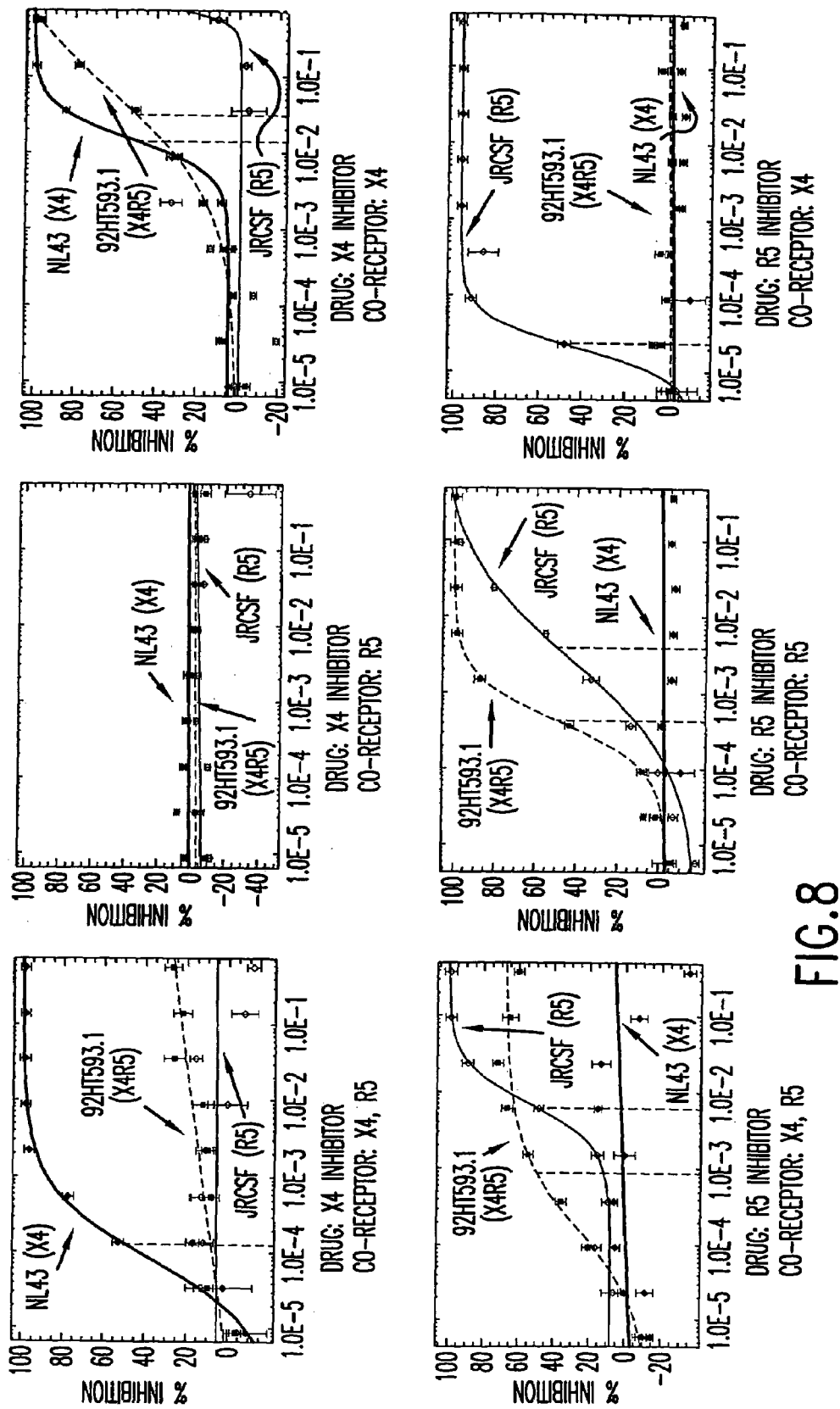

FIG. 8. Entry Inhibitor Susceptibility: CCR5 Inhibitor Inhibition is shown following administration of co-receptor antagonists.

Figure 9:
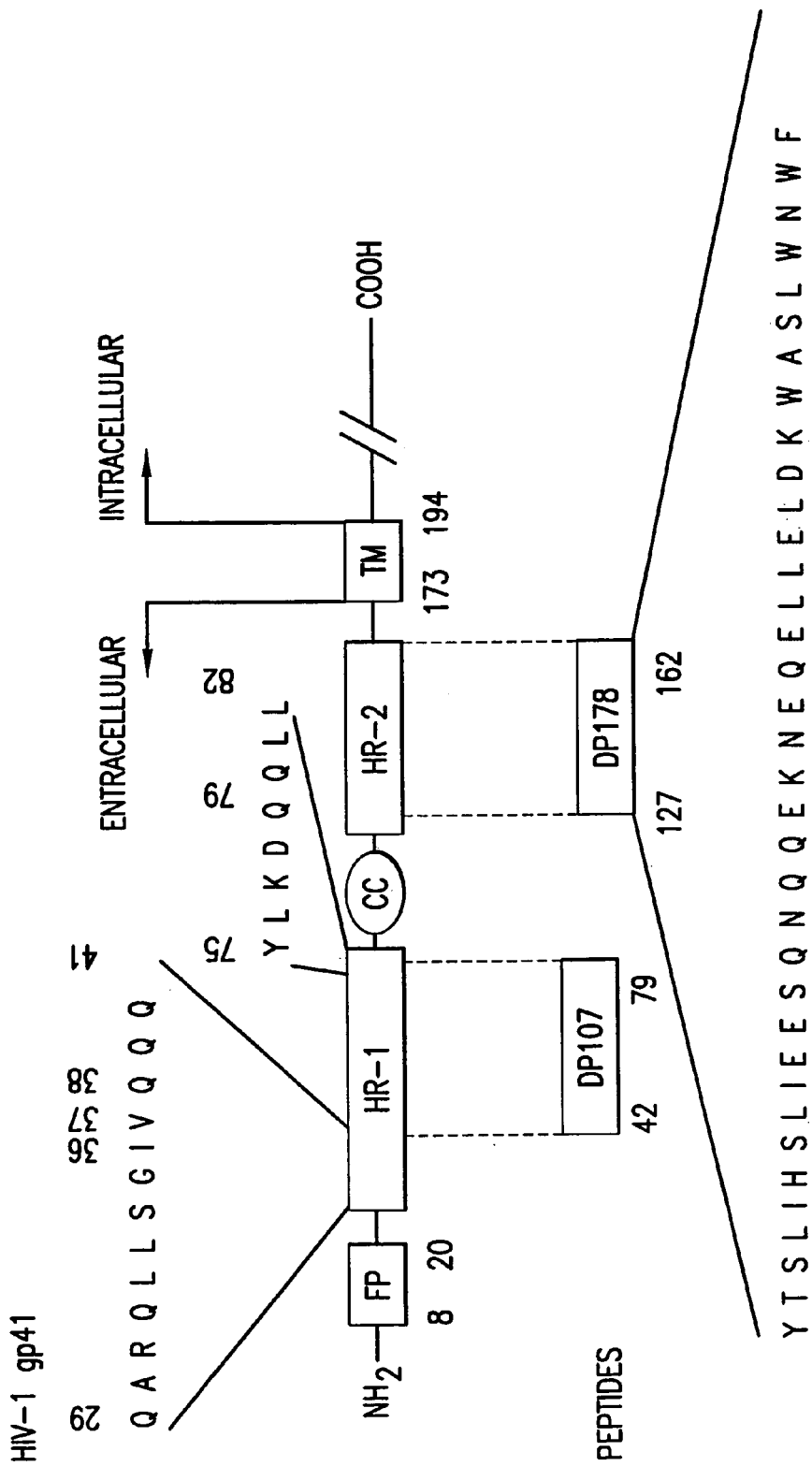

FIG. 9. Entry inhibitor susceptibility: CXCR4 Inhibitor Map and amino acid sequence is shown for a peptide which is an inhibitor of fusion between a viral membrane and a cell membrane.

FIG. 10. Inhibition by Co-Receptor Antagonists

FIG. 11. T20 Resistance Mutations

FIG. 12. Identifying Entry Inhibitor Resistance Mutations

FIG. 13. Fusion Inhibitor Peptides

The invention in its particular features can become more apparent from the following detailed description considered with reference to the accompanying figures and examples. The following description discusses the means and methods to carry out the present invention pertaining to a phenotypic assay relating to identifying and evaluating inhibitors of viral entry, including for example, and not as a limitation to the present invention, HIV-1 and inhibitors to HIV-1 viral entry.

DETAILED DESCRIPTION OF THE INVENTION

This invention provides a method for identifying whether a compound inhibits entry of a virus into a cell which comprises: (a) obtaining nucleic acid encoding a viral envelope protein from a patient infected by the virus; (b) co-transfecting into a first cell (i) the nucleic acid of step (a), and (ii) a viral expression vector which lacks a nucleic acid encoding an envelope protein, and which comprises an indicator nucleic acid which produces a detectable signal, such that the first cell produces viral particles comprising the envelope protein encoded by the nucleic acid obtained from the patient; (c) contacting the viral particles produced in step (b) with a second cell in the presence of the compound, wherein the second cell expresses a cell surface receptor to which the virus binds; (d) measuring the amount of signal produced by the second cell in order to determine the infectivity of the viral particles; and (e) comparing the amount of signal measured in step (d) with the amount of signal produced in the absence of the compound, wherein a reduced amount of signal measured in the presence of the compound indicates that the compound inhibits entry of the virus into the second cell.

In one embodiment of this invention, the indicator nucleic acid comprises an indicator gene. In another embodiment of this invention, the indicator gene is a luciferase gene.

In one embodiment of this invention, the cell surface receptor is CD4. In one embodiment of this invention, the cell surface receptor is a chemokine receptor. In one embodiment of this invention, the cell surface receptor is CXCR4 or CCR5.

In one embodiment of this invention, the patient is infected with the HIV-1 virus, a hepatitis virus (such as the HCV or HBV virus), or any other virus.

In one embodiment of this invention, the nucleic acid of step (a) comprises DNA encoding gp120 and gp41.

In one embodiment of this invention, the viral expression vector comprises HIV nucleic acid.

In one embodiment of this invention, the viral expression vector comprises an HIV gag-pol gene.

In one embodiment of this invention, the viral expression vector comprises DNA encoding vif, vpr, tat, rev, vpu, and nef.

In one embodiment of this invention, the first cell is a mammalian cell.

In one embodiment of this invention, the mammalian cell is a human cell.

In one embodiment of this invention, the human cell is a human embryonic kidney cell.

In one embodiment of this invention, the human embryonic kidney cell is a 293 cell.

In one embodiment of this invention, the second cell is a human T cell.

In one embodiment of this invention, the second cell is a human T cell leukemia cell line.

In one embodiment of this invention, the second cell is a peripheral blood mononuclear cell.

In one embodiment of this invention, the second cell is an astroglioma cell.

In one embodiment of this invention, the astroglioma cell is a U87 cell.

In one embodiment of this invention, the second cell is a human osteosarcoma cell.

In one embodiment of this invention, the human osteosarcoma cell is an HT4 cell.

In one embodiment of this invention, the compound binds to the cell surface receptor.

In one embodiment of this invention, the compound is a ligand of the cell surface receptor.

In one embodiment of this invention, the compound comprises an antibody.

In one embodiment of this invention, the compound inhibits membrane fusion.

In one embodiment of this invention, the compound is a peptide, a peptidomimetic, an organic molecule, or a synthetic compound.

In one embodiment of this invention, the compound binds the viral envelope protein.

This invention provides for a method for making a composition which comprises admixing the compound identified by the screening method (method for identifying a compound) described herein with a carrier.

In one embodiment of this invention, the carrier is saline, polyethylene glycol, a buffer solution, a starch, or an organic solvent.

The invention provides for a method for identifying a cell surface receptor which is bound by a virus upon infection of a cell by the virus which comprises: (a) obtaining viral particles which comprise (i) a viral nucleic acid and (ii) an indicator nucleic acid which produces a detectable signal; (b) contacting a cell which expresses a cell surface receptor with the viral particles from step (a); and (c) measuring the amount of detectable signal produced within the cell, wherein production of the signal indicates the cell surface receptor expressed by the cell is bound by the virus, thereby identifying the cell surface receptor as being bound by the virus upon infection of the cell.

The invention also provides for a method for identifying whether an antibody inhibits entry of a virus into a cell which comprises: (a) obtaining nucleic acid encoding a viral envelope protein from a patient infected by the virus; (b) co-transfecting into a first cell (i) the nucleic acid of step (a), and (ii) a viral expression vector which lacks a nucleic acid encoding an envelope protein, and which comprises an indicator nucleic acid which produces a detectable signal, such that the first cell produces viral particles comprising the envelope protein encoded by the nucleic acid obtained from the patient; (c) contacting the viral particles produced in step (b) with a second cell in the presence of the antibody, wherein the second cell expresses a cell surface receptor to which the virus binds; (d) measuring the amount of signal produced by the second cell in order to determine the infectivity of the viral particles; and (e) comparing the amount of signal measured in step (d) with the amount of signal produced in the absence of the compound, wherein a reduced amount of signal measured in the presence of the antibody indicates that the antibody inhibits entry of the virus into the second cell.

The invention provides for a method for determining susceptibility of a virus to a compound which inhibits viral cell entry which comprises: (a) obtaining nucleic acid encoding a viral envelope protein from a patient infected by the virus; (b) co-transfecting into a first cell (i) the nucleic acid of step (a), and (ii) a viral expression vector which lacks a nucleic acid encoding an envelope protein, and which comprises an indicator nucleic acid which produces a detectable signal, such that the first cell produces viral particles comprising the envelope protein encoded by the nucleic acid obtained from the patient; (c) contacting the viral particles produced in step (b) with a second cell in the presence of the compound, wherein the second cell expresses a cell surface receptor to which the virus binds; (d) measuring the amount of signal produced by the second cell in order to determine the infectivity of the viral particles; and (e) comparing the amount of signal measured in step (d) with the amount of signal produced in the absence of the compound, wherein a reduced amount of signal measured in the presence of the compound indicates that the virus is susceptible to the compound.

The invention provides a method for determining resistance of a virus to a compound which inhibits viral entry into a cell which comprises:(a) determining susceptibility of a virus to a compound according to the method of claim 33, wherein a nucleic acid encoding a viral envelope protein is obtained from a patient at a first time; (b) determining susceptibility of the virus to the compound according to the method of claim 33, wherein the nucleic acid encoding the viral envelope protein is obtained from the patient at a later second time; and (c) comparing the susceptibilities determined in steps (a) and (b), wherein a decrease in susceptibility at the later second time indicates resistance of the virus to the compound.

The invention provides for a method for identifying a mutation in a virus that confers resistance to a compound that inhibits viral entry into a cell which comprises: (a) determining the nucleic acid sequence or the amino acid sequence of the virus prior to any treatment of the virus with the compound; (b) obtaining a virus resistant to the compound; (c) determining the nucleic acid sequence or the amino acid sequence of the resistant virus from step (b); and (d) comparing the nucleic acid sequence or the amino acid sequences of steps (a) and (c), respectively, so as to identify the mutation in the virus that confers resistance to the compound.

In one embodiment of this invention, the virus obtained in step (b) is the virus of step (a) grown in the presence of the compound until resistance is developed.

In one embodiment of this invention, the virus obtained in step (b) is isolated from a patient which has been undergoing treatment with the compound.

In a preferred embodiment, this invention provides a means and method for accurately and reproducibly measuring the susceptibility of HIV-1 to virus entry inhibitors.

In another preferred embodiment, this invention also provides a means and method for accurately and reproducibly measuring HIV-1 co-receptor tropism.

In a preferred embodiment, this invention provides a means and method for accurately and reproducibly measuring antibody mediated neutralization of HIV-1.

In a preferred embodiment, this invention further provides a means and method for discovering, optimizing and characterizing novel or new drugs that target various defined and as yet undefined steps in the virus attachment and entry process.

In a preferred embodiment, this invention further provides a means and method for discovering, optimizing and characterizing HIV-1 vaccines (either preventative or therapeutic) that target various defined and as yet undefined steps in the virus attachment and entry process.

In a preferred embodiment, this invention provides a means and method for identifying amino acid substitutions/mutations in HIV-1 envelope proteins (gp41TM and gp120SU) that alter susceptibility to inhibitors of virus entry.

In a preferred embodiment, this invention provides a means and method for quantifying the affect that specific mutations in HIV-1 envelope have on virus entry inhibitor susceptibility.

In a preferred embodiment, this invention further provides a means and method for determining HIV-1 envelope amino acid substitutions/mutations that are frequently observed, either alone or in combination, in viruses that exhibit altered susceptibility to virus entry inhibitors.

In a preferred embodiment, this invention provides a means and method for identifying amino acid substitutions/mutations in HIV-1 envelope proteins (gp41TM and gp120SU) that alter receptor or co-receptor tropism.

In a preferred embodiment, this invention provides a means and method for quantifying the affect that specific mutations in HIV-1 envelope have receptor or co-receptor tropism.

In a preferred embodiment, this invention further provides a means and method for identifying HIV-1 envelope amino acid substitutions/mutations that are frequently observed, either alone or in combination, in viruses that exhibit CXCR4 or CCR5 co-receptor tropism.

In a preferred embodiment, this invention provides a means and method for identifying amino acid substitutions/mutations in HIV-1 envelope proteins (gp41TM and gp120SU) that alter antibody mediated neutralization.

In a preferred embodiment, this invention provides a means and method for quantifying the affect that specific mutations in HIV-1 envelope have on antibody mediated neutralization.

In a preferred embodiment, this invention further provides a means and method for identifying HIV-1 envelope amino acid substitutions/mutations that are frequently observed, either alone or in combination, in viruses that exhibit antibody medicated virus neutralization.

In a preferred embodiment, this invention further provides a means and method to identify antibodies that are frequently observed in patient samples viruses that are capable of neutralizing HIV-1.

In a preferred embodiment, this invention further provides a means and method for identification of viruses that require CD4 binding for infection.

In a preferred embodiment, this invention further provides a means and method for the identification of viruses that do not require CD4 binding for infection.

In a preferred embodiment, this invention also provides a means and method for identifying the incidence of patient samples that exhibit CD4 independent infection.

In a preferred embodiment, this invention further provides a means and method for identification of viruses that require CD8 binding for infection.

In a preferred embodiment, this invention also provides a means and method for identifying the incidence of patient viruses that exhibit CD8 dependent infection.

In a preferred embodiment, this invention further provides the means and method for the identification of viruses that require the CXCR4 chemokine receptor binding, the CCR5chemokine receptor binding, or either CXCR4 or CCR5 binding (dual tropic) for infection.

In a preferred embodiment, this invention further provides a means and method for identifying the incidence of viruses that require the CXCR4 chemokine receptor binding, the CCR5chemokine receptor binding, or either CXCR4 or CCR5 binding (dual tropic) for infection.

In a preferred embodiment, this invention further provides a means and method for identifying HIV-1 envelope amino acid substitutions/mutations that are frequently observed, either alone or in combination, in viruses that exhibit (a) altered susceptibility to virus entry inhibitors, (b) CXCR4 or CCR5 co-receptor tropism, and (c) antibody medicated virus neutralization.

In a preferred embodiment, this invention provides a means and method for using virus entry inhibitor susceptibility to guide the treatment of HIV-1.

In a preferred embodiment, this invention further provides a means and method for using virus entry inhibitor susceptibility to guide the treatment of patients failing antiretroviral drug treatment.

In a preferred embodiment, this invention further provides the means and methods for using virus entry inhibitor susceptibility to guide the treatment of patients newly infected with HIV-1.

In a preferred embodiment, this invention provides a means and method for using HIV-1 co-receptor tropism to guide the treatment of HIV-1 or to guide the treatment of patients failing antiretroviral drug treatment.

In a preferred embodiment, this invention further provides the means and method for using HIV-1 co-receptor tropism to guide the treatment of patients newly infected with HIV-1.

In a preferred embodiment, this invention further provides a means and method for measuring antibody mediated neutralization of HIV-1 to monitor the initial protective antibody response following vaccination.

In a preferred embodiment, this invention further provides a means and method for measuring antibody mediated neutralization of HIV-1 to monitor the initial therapeutic antibody response following vaccination.

In a preferred embodiment, this invention further provides a means and method for measuring antibody mediated neutralization of HIV-1 over time to monitor the durability of a protective antibody response following vaccination.

In a preferred embodiment, this invention further provides a means and method for measuring antibody mediated neutralization of HIV-1 to develop and optimize vaccination prime-boost schedules that maximize vaccination potency and durability.

For example, in the case of HIV-1, the SU protein (gp120-SU) is tightly associated with the transmembrane envelope protein (gp41-TM) that anchors the complex to the virus membrane. The envelope proteins gp120 and gp41 are derived by cleavage of gp160, the uncleaved precursor product of the envelope gene. The binding of HIV-1 to its cellular receptor (CD4) and co-receptor (either CCR5 or CXCR4) promotes conformational changes in the TM protein resulting in the fusion of the viral and cellular membrane and entry of the virus core into the cytoplasm (Retroviruses, 1997). Although the new HIV entry inhibitors target either viral envelope proteins (gp120/gp41) or host proteins (CD4, CCR5, CXCR4), the majority of resistance-associated mutations in HIV-1 are expected to be located in the viral envelope gene; e.g. one likely way viruses might evolve is to shift co-receptor utilization. Entry blockers constitute a novel class of anti-retroviral drugs, and the potential for broad activity against current multi-drug resistant HIV-1 variants is high. Among the class of potential viral entry blockers are fusion inhibitors, receptor/co-receptor antagonists and vaccines.

Nonetheless, inhibitors of viral entry are likely to generate drug resistant viruses (through mutation of the envelope gene), thus complicating patient treatment similar to that observed for protease inhibitor (PRI) and reverse transcriptase inhibitor (RTI) treatment for HIV. In fact, FDA approval of any new drug that blocks viral entry will require the evaluation of resistance data. The need for a diagnostic assay that measures susceptibility to entry blockers has been documented in the case of the fusion inhibitor T-20. Viruses exhibiting reduced susceptibility to T-20 have been reported after passage in vitro in the presence of the drug. At this time, convenient phenotypic assays that are capable of measuring susceptibility to drugs that block viral entry are not available. Consequently physicians will soon be faced with the challenge of tailoring therapy in the absence of the tools necessary to address drug susceptibility. Therefore, a reliable assay that accurately measures susceptibility to drugs that inhibit viral entry from infected patients would be extremely valuable.

For example, recent World Health Organization estimates indicate that worldwide more than 33 million people are infected with HIV-1, the causative agent for the AIDS pandemic. Nearly one million people are infected in the United States and 300,000 are currently receiving anti-viral therapy (CDC, 1999; WHO 1999). Combating AIDS has become the common goal of an unprecedented effort of governmental agencies, academic laboratories, and the pharmaceutical/biotechnology industry. Fourteen anti-viral drugs have been approved by the FDA for treatment of HIV-1 infection (carpenter et al., 2000) and more than 20 additional drugs are currently being evaluated in clinical trials (PHRMA, 1999). The approved drugs inhibit HIV-1 replication by interfering with the enzymatic activities of either protease (PR) or reverse transcriptase (RT). PR inhibitors (PRIs) block the proper formation of viral proteins that are necessary for virus infection and replication, while RT inhibitors (RTIs) block the virus from copying its genetic material. Due to sub-optimal potency, current PRIs and RTIs are most often used in combination to suppress viral replication (Carpenter et al., 2000).

What is desired, therefore, is to provide a rapid, accurate safe viral assay capable of evaluating:

33. the activity of inhibitors of viral attachment and entry (including fusion, receptor and co-receptor inhibitors);
34. receptor/co-receptor viral tropism to facilitate viral entry inhibitor drug design and treatment;
35. changes in drug susceptibility of patient viruses to inhibitors of attachment and entry; and
36. viral neutralizing activity generated in response to vaccination using viral envelope protein antigens.

The methods of this invention can be used for any viral disease that may be responsive to a viral entry inhibitor and where anti-viral drug susceptibility and resistance to a viral entry inhibitor is a concern including, for example, including, but not limited to other lentiviruses (e.g. HIV-2), other retroviruses (e.g. HTLV-1 and 2), hepadnaviruses (e.g. human hepatitis B virus), flaviviruses (e.g. human hepatitis C virus) and herpesviruses (e.g. human cytomegalovirus).

Entry blockers constitute a novel class of anti-retroviral drugs, and the potential for broad activity against current multi-drug resistant HIV-1 variants is high. Among the class of potential viral entry blockers are fusion inhibitors, receptor/co-receptor antagonists and vaccines.

Fusion Inhibitors

Compounds designed to competitively inhibit the conformational change of TM, designated fusion inhibitors, are potent inhibitors of HIV-1 replication. Although their activity has been demonstrated both in cell culture systems and HIV-1 infected patients (Wild et al., 1992; Judice et al., 1997; Kilby et al., 1998), no fusion inhibitor has yet been approved for the treatment of HIV-1 infection in the U.s. Drugs within this class, such as t-20 and t-1249 (Trimeris Inc., USA), are the subject of advanced clinical investigations.

Receptor/Co-receptor Antagonists

In addition to fusion inhibitors, which act after HIV-1 has interacted with its receptors, efforts are in progress to develop drugs that prevent HIV-1 from interacting with CD4 or either of its two principal co-receptors. The ability of such reagents to inhibit HIV-1 infection has been demonstrated in cell culture systems and animal models. Lead compounds targeting either gp120, CD4, the CCR5 co-receptor used by macrophage tropic viruses (R5), or the CXCR4 co-receptor used by T-cell tropic viruses (X4) have been identified (Allaway et al., 1993; Reimann et al., 1995; Baba et al., 1999; Bridger et al., 1999).

Currently, no co-receptor antagonists are approved for the treatment of HIV-1 infection in the U.S. Drugs within these classes, such as PRO 542 (Progenics Inc., USA), 5a8 (Tanox, USA), TAK-779 (Takeda Inc., Japan), and AMD-3100 (Anormed Inc., Canada), are the subjects of preclinical or early stage clinical investigations. Therefore, an assay capable of identifying and determining receptor/co-receptor tropism, which quickly and accurately identifies patients that are infected with strains of a tropic virus (e.g. HIV-1), would facilitate viral entry inhibitor drug design and treatment.

Vaccines

Vaccines have also proven to be an effective strategy in the fight against pathogenic viral infections in humans, and several vaccine candidates to prevent HIV-1 infection are in clinical development. The envelope proteins gp120 and gp41 are the most obvious candidates in the intense search for an HIV-1 vaccine, and many of the 11 vaccine candidates in clinical evaluation are envelope-based (PhRMA, 1999). It is generally thought that an effective envelope vaccine may elicit the generation of neutralizing antibodies that block viral infection (Mascola et al., 2000). Therefore, a sensitive high-throughput assay that reliably measures the efficacy of such neutralizing antibodies and does not require prolonged cultivation of virus is urgently needed. Such an assay could significantly aid the search for an effective AIDS vaccine. This is particularly true, considering that late-stage clinical trials encompass large patient populations numbering in the thousands. Since neutralizing antibodies should prevent successful infection of target cells, a envelope receptor assay would be beneficial to serve as a virus neutralization assay.

Unfortunately, most of these drug combinations are effective for only a limited time in large part due to the emergence of drug resistant viruses. The lack of proofreading functions inherent to RT and RNA polymerase II, coupled with high level, error-prone replication allows viruses such as HIV-1 to mutate readily (Coffin, 1995). This high mutation frequency contributes to the ability of HIV-1 to evade successful long-term drug therapy, resulting in viral load rebound. Resistance-associated mutations to all of the 14 approved drugs as well as to many investigational compounds have been described (Schinazi et al., 1999). Consequently, multi-drug resistant HIV-1 variants pose an increasing problem in the care of infected patients. To achieve long-term clinical benefit, it is desirable to select those drugs that maximally suppress viral replication and avoid the drugs to which a patient's virus is resistant (DHHs, 2000). Long-term solutions can rely on drug resistance tests that can guide physicians in selecting the most effective drugs against the patient's virus. The need for resistance testing has been affirmed in recent guidelines from the DHHs (DHHs, 2000), recommending that resistance tests be routinely used when treating HIV-1 infected patients. Susceptibility tests can also assist in the development of new drugs that target resistant viruses. A recent FDA advisory committee (November 1999) recommended that resistance testing be used in the development of new anti-viral drugs for HIV-1.

Several strategies have been applied to the assessment of antiviral drug susceptibility. Genotypic tests analyze mutations in the underlying nucleotide sequence, or genotype, and attempt to correlate these mutations with drug resistance (Rodriguez-Rosado et al., 1999; Schinazi et al, 1999). However, the relationship between genotype and phenotype is complex and not easily interpreted, and the results of these tests are not quantitative. The use of genotypic drug susceptibility data requires interpretation either by experts (Baxter et al., 1999) or computer algorithms and are not always predictive of treatment outcome (Piketty et al., 1999).

Phenotypic drug susceptibility assays directly measure and quantify the ability of viruses to replicate in the presence of drug. Early phenotypic tests required prolonged virus cultivation and consequently were slow, labor intensive, and not easily automated for high throughput (Japour et al., 1993). As a result, these early phenotypic tests were considered impractical for patient management. The development of recombinant virus assays (Shi and Mellors, 1997; Hertogs et al., 1998) simplified phenotypic testing and increased throughput. However, a major disadvantage of these assays is a lengthy turnaround time of 4-8 weeks. More recently, recombinant virus assays have been developed and others that are capable of measuring drug susceptibility during a single round of replication (Zennou et al., 1998; Petropoulos et al., 2000), resulting in a dramatic reduction in turnaround time to 8-10 days. Patients failing anti-retroviral therapy can benefit from phenotypic assays. Such assays are attractive tools for patient management because they provide a direct and rapid measure of drug susceptibility.

The assay of this invention can be used with other viral infections arising from infections due to other viruses within these families as well as viral infections arising from viruses in other viral families. In addition, the drug susceptibility and resistance test of this invention is useful for screening for compounds to treat viral diseases for which there is no currently available therapy.

The structure, life cycle and genetic elements of the viruses which could be tested in the drug susceptibility and resistance test of this invention would be known to one of ordinary skill in the art. It is useful to the practice of this invention, for example, to understand the life cycle of a retrovirus, as well as the viral genes required for retrovirus rescue and infectivity. Retrovirally infected cells shed a membrane virus containing a diploid RNA genome. The virus, studded with an envelope glycoprotein (which serves to determine the host range of infectivity), attaches to a cellular receptor in the plasma membrane of the cell to be infected. After receptor binding, the virus is internalized and uncoated as it passes through the cytoplasm of the host cell. Either on its way to the nucleus or in the nucleus, the reverse transcriptase molecules resident in the viral core drive the synthesis of the double-stranded DNA provirus, a synthesis that is primed by the binding of a tRNA molecule to the genomic viral RNA. The double-stranded DNA provirus is subsequently integrated in the genome of the host cell, where it can serve as a transcriptional template for both mRNAs encoding viral proteins and virion genomic RNA, which will be packaged into viral core particles. On their way out of the infected cell, core particles move through the cytoplasm, attach to the inside of the plasma membrane of the newly infected cell, and bud, taking with them tracts of membrane containing the virally encoded envelope glycoprotein gene product. This cycle of infection—reverse transcription, transcription, translation, virion assembly, and budding—repeats itself over and over again as infection spreads.

The viral RNA and, as a result, the proviral DNA encode several cis-acting elements that are vital to the successful completion of the viral lifecycle. The virion RNA carries the viral promoter at its 3' end. Replicative acrobatics place the viral promoter at the 5' end of the proviral genome as the genome is reverse transcribed. Just 3' to the 5' retroviral LTR lies the viral packaging site. The retroviral lifecycle requires the presence of virally encoded transacting factors. The viral-RNA-dependent DNA polymerase (pol)—reverse transcriptase is also contained within the viral core and is vital to the viral life cycle in that it is responsible for the conversion of the genomic RNA to the integrative intermediate proviral DNA. The viral envelope glycoprotein, env, is required for viral attachment to the uninfected cell and for viral spread. There are also transcriptional trans-activating factors, so called transactivators, that can serve to modulate the level of transcription of the integrated parental provirus. Typically, replication-competent (non-defective) viruses are self-contained in that they encode all of these trans-acting factors. Their defective counterparts are not self-contained.

In the case of a DNA virus, such as a hepadnavirus, understanding the life cycle and viral genes required for infection is useful to the practice of this invention. The process of HBV entry has not been well defined. Replication of HBV uses an RNA intermediate template. In the infected cell the first step in replication is the conversion of the asymmetric relaxed circle DNA (rc-DNA) to covalently closed circle DNA (cccDNA). This process, which occurs within the nucleus of infected liver cells, involves completion of the DNA positive-strand synthesis and ligation of the DNA ends.

In the second step, the cccDNA is transcribed by the host RNA polymerase to generate a 3.5 kB RNA template (the pregenome). This pregenome is complexed with protein in the viral core. The third step involves the synthesis of the first negativesense DNA strand by copying the pregenomic RNA using the virally encoded P protein reverse transcriptase. The P protein also serves as the minus strand DNA primer. Finally, the synthesis of the second positive-sense DNA strand occurs by copying the first DNA strand, using the P protein DNA polymerase activity and an oligomer of viral RNA as primer. The pregenome also transcribes mRNA for the major structural core proteins.

Design and Methods

37) Construction of an Expression Vector for a Viral Envelope Protein that is Capable of Accepting Patient-derived Segments Encoding the Envelope Protein.

In one embodiment, an envelope expression vector capable of expressing HIV-1 envelope proteins in transfected cells was constructed. Similar expression vectors have been described, including a plasmid (pAmphoEnv) constructed to express amphotropic murine leukemia virus (A-MLV) envelope protein as described in U.S. Pat. No. 5,837,464 and (Petropoulos et al., 2000). The pAmphoEnv vector uses the immediate early gene promoter of human cytomegalovirus (CMV) and the SV40 polyadenlyation signal sequence to produce A-MLV envelope mRNA in transfected cells. The pAmphoEnv plasmid is modified by deleting the A-MLV envelope gene and introducing restriction enzyme cleavage sites that can enable the insertion of viral envelope fragments derived from a variety of isolates, such as HIV-1. In the case of, HIV-1, the envelope open reading frame spans approximately 2,600 nucleotides and encodes the envelope polyprotein, gp160 The gp160 polyprotein is cleaved by a cellular furin-like protease to produce two subunits, gp41 and gp120. HIV-1 envelope expression vectors can be constructed in stages as follows:

(a) Replacing the A-MLV Envelope Nucleic Acid Sequences from the Envelope Expression Vector (pAmphoEnv) with a Multiple Cloning Site Polylinker:

The A-MLV envelope nucleic acid sequences can be deleted from the pAmphoEnv vector by restriction enzyme digestion. The digested vector can be re-circularized by ligation to a duplex oligonucleotide polylinker containing four unique internal restriction sites (a, b, c, d) for insertion of envelope sequences. The ligation reaction can be used to transform *Escherichia Coli* and molecular clones containing the correct polylinker sequence can be identified and confirmed by restriction mapping and DNA sequencing, respectively. The introduction of multiple unique cloning sites into the vector can facilitate the insertion of HIV-1 envelope sequences. Restriction sites within the polylinker can be chosen based on their infrequent occurrence in HIV-1 envelope sequences (LANL HIV-1 database, www.lanl.gov). This vector can be referred to as pCX. The functionality of the pCX vector can be demonstrated by inserting a reporter gene or indicator nucleic acid, such as firefly luciferase, into the pCX multiple cloning site and measuring a signal from the indicator nucleic acid or reporter gene activity in transfected cells. As used herein, "indicator nucleic acid" refers to a nucleic acid encoding a protein, DNA or RNA structure that either directly or through a reaction gives rise to a measurable or noticeable signal, e.g. color or light of measurable wavelength, or generation of a specific DNA or RNA structure used as an indicator which could be amplified using any one of a number of quantitative amplification assays.

(b) Inserting Viral Envelope Sequences into the pCX Envelope Expression Vector:

Using mutagenic primers for PCR amplification, viral envelope fragments are generated that contain two unique restriction sites (a, b and c, d, respectively) adjacent to the initiation and termination codons of, for example, the HIV-1 envelope open reading frame. Introduction of two unique restriction sites at each end of the envelope open reading frame can improve chances of cloning HIV-1 envelope fragments harboring internal restriction sites for any one of the enzymes found in the multiple cloning site of the pCX vector.

In the case of HIV-1, two well-characterized molecular clones of HIV-1 with known differences in the envelope gene, NL4-3 (a syncytium-inducing, T-cell tropic, laboratory strain) and JR-CSF (a non-syncytium-inducing, macrophage-tropic, primary isolate) can be used as template for PCR amplification. The 2,600 nucleotide amplification products can be digested with two restriction enzymes (each enzyme cleaving at one end of the fragment; e.g. a and c or b and d) and subsequently inserted into the pCX vector by ligation and transformation of Escherichia Coli. Molecular clones containing the appropriate envelope sequences can be identified by restriction mapping and confirmed by DNA sequencing. The resulting plasmids, pHIVenv (NL4-3) and pHIVenv (JR-CSF), can be used to express HIV-1 envelope proteins in transfected cells (FIG. 1A). The functionality of the envelope expression vectors, such as the pHIVenv vectors, can be demonstrated by measuring viral envelope synthesis in transfected cells (Western Blot), and by their ability to pseudotype envelope deficient retrovirus vectors. High titer virus stocks using the human embryonic kidney 293 cell line has been demonstrated (Petropoulos et al., 2000), however the present invention is not restricted to those cell lines. Other suitable cell lines used as a first cell for transfection of nucleic acid obtained from the patient encoding a viral envelope protein include, by way an example and not as limitation to the present invention, 5.25; HOX; U87; MT2; PM1 CEM; etc. The cell line optimally will be engineered to express one or more co-receptors.

(c) Modifying the pCX Vector to Improve the Efficiency of Cloning Viral Envelope Sequences:

To improve the cloning efficiency of viral envelope fragments, the pCX expression vector can be modified by inserting a bacterial killer gene cassette (e.g. control of c̲ell death b̲ gene (ccdB) or a member of the hok-killer gene family) under the control of the Escherichia Coli lac promoter into the multiple cloning site (the et al., 1990; Bernard and Couturier, 1992; Bernard et al., 1993). This modified vector is referred to as pCXccdB. Transcription of the ccdB killer gene is repressed in bacterial strains that express the laci$^q$ repressor, such as JM109. This or an equivalent strain can be used to propagate plasmids carrying the ccdB killer gene that are under the control of the lac promoter. Conversely, in this system bacterial strains that do not overexpress the laci$^q$ repressor, such as DH5á and Top10, cannot maintain plasmids that express the ccdB gene. Transformants can be killed due to the ccdB activity. DH5á and Top10 cells can be purchased from several vendors (Life Technologies or Invitrogen). Using this selective cloning approach, the parental expression vector is propagated in a laci$^q$ bacterial strain. The vector is digested with two restriction enzymes that both remove the ccdB gene cassette, and, in the case of HIV-1, are compatible with the insertion of HIV-1 envelope sequences (a, b, c, d). Following ligation of the vector and envelope fragments, a strain of bacteria lacking laci$^q$ is transformed. Once transformed, bacteria containing plasmids in which the viral envelope inserts have replaced the ccdB killer gene can grow. Bacteria containing plasmids that retain or reconstitute the ccdB killer gene can not survive. In this way, the population of transformed bacteria is enriched for plasmids that contain viral envelope inserts, but is lacking in the parental vector containing the ccdB gene. The construction of the pCXccdB vector is not essential for the success of phase I of this project, but it is expected to significantly improve the efficiency of cloning HIV-1 envelope sequences derived from patient samples; thus, the probability of maintaining the heterogeneity of viral sequences can be improved. The structure of the pCXccdB vector can be confirmed by restriction mapping and DNA sequencing.

(d) Inserting Viral Envelope Sequences into the pCXccdB Expression Vector:

The functionality of the pCXccdB vector can be evaluated by setting up ligation reactions containing viral envelope sequences and incompletely digested pCXccdB vector DNA. Following bacterial transformation, plasmid DNA can be prepared from individual bacterial clones and analyzed by restriction digestion for the presence of viral envelope fragments and the absence of ccdB sequences. The feasibility of this approach is tested by amplifying the envelope region from a total of 13 available HIV-1 clones (pCRII-91US005.11, pCRII-91006.10, pCRII-92US657.1, pCRII-92US711.14, pCRII-91US712.4, pCRII-92US714.1, pCRII-91HT652.11, pCRII-92BR020.4, pCRII-91HT651.1A, pCRII-92HT593.1, pCRII-92HT594.10, pCRII-92HT596.4, pCRII-92HT599.24), obtainable through the AIDS research reagent reference program (ARRRP), Rockville, Md. Each fragment can be inserted into pCXccdB and the structure of the resulting pHIVenv expression vectors can be confirmed by restriction mapping and/or DNA sequencing. The functionality of each pHIVenv vector can be demonstrated by measuring HIV-1 envelope protein synthesis in transfected cells (Western Blot), and by their ability to pseudotype envelope-deficient retrovirus vectors.

2) Construction of a Bio-safe Viral Expression Vector Comprising Indicator Nucleic Acid in Place of the Region Encoding the Envelope Protein.

A bio-safe viral vector is constructed to evaluate inhibitors of viral entry according to similar means and methods as described in U.S. Pat. No. 5,837,464 and Petropoulos et al., 2000 used to evaluate inhibitors of PR and RT. The viral expression vector of the present invention can be co-transfected into cells together with the envelope expression vectors (described above) to produce high titer virus stocks. Such virus stocks can be evaluated for susceptibility to inhibitors of virus entry, including antiviral drugs and neutralizing antibodies. In the case of HIV-1, the viral expression vector can be generated from NL4-3, a well-characterized infectious molecular clone of HIV-1. The 5' long terminal repeat (LTR) which controls viral gene expression can be modified so that transcription of the viral genes in transfected cells is driven by the CMV immediate early promoter (Naviaux et al., 1996). Most of the envelope gene can be deleted, but important control elements such as the rev responsive element (RRE) and accessory protein coding regions (rev, tat) are retained. In place of the deleted envelope sequences, an indicator nucleic acid, such as a firefly luciferase reporter gene cassette that is under the control of CMV promoter-enhancer sequences (FIGS. 1B and 3) is inserted. Virus infection can be monitored by measuring luciferase activity in infected cells. It is conceivable, although unlikely, that inter-plasmid recombination between the retroviral vector and, for example, the pHIVenv sequences in transfected cells may lead to the generation of infectious HIV-1. In effort to generate a biosafe vector, introduction of several genetic alterations in the HIV genome can be done. For example, deletion of most of the envelope gene, while retaining the important control sequence, RRE, and also deletion of the transcriptional enhancer sequences in the U3 region of the 3' LTR of the vector (FIG. 2) can be accomplished. During the replication of the retroviral genome, the U3 region located at the 3' end of the virus genome serves as the template for the U3 region of the 5' LTR of the provirus in infected cells. Such proviruses lack the strong promoter element in the U3 region of the 5' LTR and thus are unable to produce retroviral RNA in infected cells. This self-inactivating (SIN) strategy has been used successfully for several retroviral vector systems, including HIV-1 (Hwang et al., 1997; Miyoshi et al, 1998). In the assay of the present invention, viral gene expression is not required in infected cells because virus infection is measured by a detectable signal produced by the indicator nucleic acid, such as the production of luciferase activity, driven by its own separate promoter (FIG. 1B). Deletion of envelope sequences and the transcriptional enhancer region (U3) can be accomplished by standard molecular cloning procedures, and each deletion can be verified by DNA sequence analysis.

Functionality of this vector, for example in the case of HIV-1, designated pHIVlucÄU3, can be demonstrated by co-transfection of 293 cells with the pHIVenv vector described above. Efficient transcomplementation of viral proteins produced by both vectors in the transfected cells can lead to the production of viral particles. Virus particles can be harvested from the culture supernatants and analyzed by Western-blotting. Virus titers can be quantitated by routine applications of either p24 ELISA, quantitative PCR or TaqMan assays.

It is not necessary to produce a self-inactivating viral expression vector to carry out the present invention, but it is desirable to improve assay reproducibility and biosafety.

3) Identification of Suitable Cell Lines which Express Receptors and Co-receptors and Support Viral Infection.

Different mammalian cell lines that have been described previously and are known to support infection of a particular virus can be evaluated. As discussed herein for one embodiment relating to HIV-1, the assay can be performed by (a) co-transfecting a first cell with pHIVenv and pHIVlucÄU3, (b) harvesting virus after transfection, (c) using this virus to infect a second cell, both in the presence and absence of virus entry inhibitors, and (d) measuring luciferase production in infected cells.

Table 1 lists representative examples of such cell lines evaluated for HIV-1 infection, including the cell line and its associated receptor/co-receptor. Several of these cell lines can be obtained from public cell repositories.

Viral particles harvested from transfected 293 cell cultures can be used to infect a variety of different cell lines. In the case of HIV-1, the pHIVlucÄU3 vector contains deletions in the envelope gene and the U3 promoter-enhancer as described above, therefore infection of a permissive cell line with virus particles produced by this vector is restricted to a single round of replication. This includes (a) virus attachment and entry, mediated by the viral envelope proteins, produced in trans by the pHIVenv vector as described, (b) the conversion of single stranded viral RNA into double stranded DNA by RT, and (c) integration of viral DNA into the host cell genome (provirus formation). The active transcription of viral genes by RNA polymerase II that normally occurs in infected cells following proviral integration can be restricted by deleting essential viral promoter-enhancer sequences in the pHIVlucÄU3 vector. However, this restriction can not interfere with luciferase gene expression in infected cells since this gene is driven independently of viral gene expression using an internal CMV promoter (FIG. 1B). The amount of luciferase activity produced following infection can be used as a measure of viral infectivity.

HIV-1 attachment and entry into host cells requires interaction with a primary receptor (CD4) and one of several co-receptors, most often CCR5 or CXCR4. Cell lines can be screened that are known to express various combinations of CD4, CCR5 and CXCR4. Specifically, cell lines listed in Table 1 that express (a) CD4 plus CCR5, (b) CD4 plus CXCR4, and (c) CD4 plus CCR5 plus CXCR4 are evaluated. Cell lines that express the CD4 receptor alone, or either the CCR5 or CXCR4 co-receptor alone, may serve as useful controls and can be used to evaluate HIV-1 isolates that do not require CD4 binding or that use co-receptors other than CCR5 and CXCR4. The principal criterion for judging cell line suitability can be infectivity as measured by luciferase production ($10^4$–$10^6$ relative light units). In addition, cell lines can be evaluated based on growth rates, viability, stability and other parameters as deemed necessary. Cell lines can be selected that are easy to maintain and for example, produce large amounts of luciferase activity following infection, which can be inf the ected by different envelope receptor tropisms, e.g. CD4/CXCR4 and CD4/CCR5. Additional well-characterized cell lines that support, for example, HIV replication and express the HIV-1 receptor and co-receptors (e.g. CEM-NKr-CCR5; release category a) are available through public repositories such as the ARRRP.

Further, cell lines can be enhanced using standard procedures, such as promoting infection by the addition of polybrene to cells (Porter et al., 1998). For example, in the case of HIV, other potential cell lines can be identified for use with the present invention by infection with HIV-1 laboratory strains and comparing the recombinant virus infectivity titers to those obtained with infectious HIV-1, or by transfecting cells directly with the viral expression plasmids described herein, and scoring for virus production. Accumulation of viral transcripts can be checked by using a quantitative RT-PCR assay. Cell lines suitable for other viruses can be identified in a similar manner.

The present invention can optimize assay conditions and allow for high-throughput testing of patient samples using automation. Sample preparation methods can be optimized to efficiently capture viral genomic and envelope RNAs. RT-PCR conditions can be optimized to enable amplification of patient-derived viral envelope sequences, such as HIV-1 envelope sequences (~2,600 base pairs) at low viral loads (~500 copies per ml).

4) Demonstration of the Utility of the Assay

The utility of the assay of the present invention is demonstrated by the results achieved from: (1) testing for dose-dependent inhibition of viral entry in the presence of well-characterized inhibitors; and the (2) testing for dose-dependent inhibition of infection in the presence of well-characterized HIV-1 neutralizing antibodies.

The following applications for the virus entry assay of the present invention were evaluated:
  i) detecting inhibition of HIV-1 replication by inhibitors of virus attachment and entry (including fusion, receptor and co-receptor inhibitors);
  ii) measuring changes in susceptibility to HIV-1 attachment and entry inhibitors; and
  iii) detecting neutralization activity of antibodies generated in response to vaccines targeted against HIV-1 envelope proteins.

In a preferred embodiment, the assay can be performed by (a) co-transfecting a first cell with pHIVenv and pHIVlucÄU3 vectors, (b) harvesting virus after approximately 48 h after transfection, (c) using this virus to infect a second cell, both in the presence and absence of virus entry inhibitors and (d) measuring luciferase production approximately 48–72 hrs. after infection. Dose-dependent inhibition of HIV-1 replication can be evaluated against a wide range of virus entry inhibitor concentrations using a 96-well format. The appropriate concentration range can be determined empirically for each inhibitor. The data can be plotted as the percent inhibition of luciferase activity vs. drug concentration ($\log_{10}$). Data analysis can be performed using computer software. Inhibition curves are used to determine 50% inhibitory concentrations ($IC_{50}$) for specific drugs or antibodies (FIG. 6).

Envelope proteins derived from a variety of well-characterized HIV-1 isolates are evaluated using pHIVenv vectors constructed as described above. To define envelope co-receptor tropism, in the case of HIV-1, infection using cells expressing CD4 plus CXCR4 and CD4 plus CCR5 is evaluated as described above. A wide variety of compounds that are known to inhibit HIV-1 entry (Table 2), including non-specific agents such as sulfonated polyanions (dextran sulfate and heparin) can be used with the assay of the present invention. Chemokines such as Rantes and SDF-1, the natural ligands for the CCR5 and CXCR4 chemokine receptors, respectively (see Alkhatib et al., 1996; Bleul et al., 1996) are also suitable for use with the present invention. Further, virus entry inhibitors such as T-20 and T1249 (Trimeris, Inc.), PRO 542 (Progenics), 5a8 (Tanox) were used to evaluate utility of the assay of the present invention.

Drug toxicity in target cells are evaluated using standard viability or cytotoxicity assays (e.g. dye exclusion, MTS, ATP).

HIV-1 mutants exhibiting reduced susceptibility to the fusion inhibitor T20 (Rimsky et al., 1998) and the genetic determinants (mutations) that enable these viruses to replicate in the presence of drug map within the envelope protein (gp41-TM) have been described. To demonstrate that the assay of the present invention is capable of measuring changes in drug susceptibility (i.e. resistance), (a) pHIVenv vectors are generated that carry these mutant envelope genes, (b) first cells are co-transfected using these vectors and the pHIVlucÄU3 vector, (c) viruses bearing these mutant envelope proteins are harvested, and (d) the viruses are tested for infectivity in the presence of T20. Reduced drug susceptibility to T20 is evaluated by comparing the $IC_{50}$ of viruses bearing mutant envelope proteins to those that lack the defined drug resistance mutations. Viruses bearing envelope proteins with drug resistance mutations can exhibit higher $IC_{50}$ values than viruses bearing envelope proteins that lack drug resistance mutations, i.e. inhibition can require a higher drug concentration (equivalent to data presented in FIG. 8). Drug resistance mutations can be introduced into envelope expression vectors (pHIVenv) using standard site directed mutagenesis techniques according to standard protocols (Petropoulos et al., 2000; Ziermann et al., 2000)

It is widely accepted that effective vaccines that protect against HIV-1 infection should elicit a strong humoral immune response characterized by broadly cross-reactive neutralizing antibodies. Consequently, the serum of vaccinated individuals is routinely evaluated for the presence of high titer neutralizing antibodies targeted against the immunogen. Most recently, using the HIV-1/simian immunodeficiency virus (SIV) chimeric virus macaque model (SHIV), Mascola and colleagues have shown that passive transfer of such neutralizing antibodies led to reduced viral load after mucosal challenge (Mascola et al., 2000). The assay of the present invention can be used to rapidly and reliably determinine the viral neutralizing activity of antibodies generated in response to vaccines targeting envelope antigens, such HIV-1 envelope antigens. For example, the assay of the present invention can (a) generate pHIVenv vectors that express a variety of well-characterized envelope proteins, (b) co-transfect a first cell using these vectors and the pHIVlucÄU3 vector, (c) harvest viruses and incubate with serial dilutions of antibody preparations or vaccine serum (d) test these viruses for infectivity in a second cell. Data analysis and $IC_{50}$ determinations can be performed as described previously and in the literature. In the case of HIV-1, viruses can be selected to represent different HIV-1 genetic backgrounds (e.g. clade A, B, C, D, E, F), different cell and co-receptor tropisms (macrophage/CCR5, T-cell/CXCR4), and different envelope properties (syncytium and non-syncytium inducing, laboratory adapted growth or primary isolate) (Table 2). It can be beneficial to prepare stocks of a defined titer from each virus to optimize assay sensitivity and reproducibility by using a virus input of approximately 20–100 $TCID_{50}$/well and making adjustments as necessary. Antibody preparations can be selected based on previously documented neutralization properties, either functional, such as their ability to neutralize primary isolates, or physical, such as their ability to bind specific gp120 or gp41 epitopes (Table 2). The performance of the assay of the present invention can be judged against the activity of these well-characterized antibody reagents in conventional virus neutralization assays as described in the scientific literature. Serum from a broadly representative group of HIV-1 infected individuals can be used to establish an appropriate range of serum dilutions that can maximize assay sensitivity, yet minimize cytotoxicity. Cytoxicity can be evaluated using standard viability or cytotoxicity assays (e.g. dye exclusion, MTS, ATP).

The following examples are presented to further illustrate and explain the present invention and should not be taken as limiting in any regard.

EXAMPLE 1

Measuring Phenotypic Drug Susceptibility to Inhibitors of HIV-1 Entry

This example provides a means and method for accurately and reproducibly measuring susceptibility to inhibitors of HIV-1 attachment and entry (heretofore collectively referred to as entry). Based on this example, the means and method for measuring susceptibility to inhibitors of HIV-1 entry can be adapted to other viruses, including, but not limited to other lentiviruses (e.g. HIV-2), other retroviruses (e.g. HTLV-1 and 2), hepadnaviruses (human hepatitis B virus), flaviviruses (human hepatitis C virus) and herpesviruses (human cytomegalovirus). This example further provides a means and method for measuring alterations (increases and decreases) in susceptibility to entry inhibitors.

Measurements of entry inhibitor susceptibility are carried out using adaptations of the means and methods for phenotypic drug susceptibility and resistance tests described in U.S. Pat. No. 5,837,464 (International Publication Number WO 97/27319) which is hereby incorporated by reference. One vector, an example of the envelope expression vector, (pHIVenv) is designed to express the envelope polyprotein (gp160) encoded by patient derived HIV envelope sequences (FIG. 1). Gp160 is subsequently cleaved by a cellular protease to generate the surface (gp120SU) and transmembrane (gp41TM) subunits that comprise the envelope protein on the surface of HIV-1 virus particles. A second vector, an example of the viral expression vector, (either pHIVluc or pHIVluc U3) is designed to express genomic and subgenomic viral RNAs and all HIV proteins except the envelope polyprotein (FIGS. 1A–1B).

In this application, patient-derived segment(s) correspond to the coding region (~2.5 kB) of the HIV-1 envelope polyprotein (gp160) and represent either (a) envelope sequences amplified by the reverse transcription-polymerase chain reaction method (RT-PCR) using viral RNA isolated from virus derived from HIV-infected individuals, or (b) envelope sequences derived from molecular clones of HIV-1 that contain specific mutations introduced by site directed mutagenesis of a parental molecular clone (typically NL4-3).

Isolation of viral RNA was performed using standard procedures (e.g. RNAgents Total RNA Isolation System, Promega, Madison WI or RNAzol, Tel-Test, Friendswood, Tex.). The RT-PCR protocol was divided into two steps. A retroviral reverse transcriptase [e.g. Superscript II (Invitrogen, Life Technologies) Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to copy viral RNA into first strand cDNA. The cDNA was then amplified to high copy number using a thermostable DNA polymerase [e.g. Taq (Roche Molecular Systems, Inc., Branchburg, N.J.), Tth (Roche Molecular Systems, Inc., Branchburg, N.J.), PrimeZyme (isolated from Thermus brockianus, Biometra, Gottingen, Germany)] or a combination of thermostable polymerases as described for the performance of "long PCR" (Barnes, W. M., (1994) Proc. Natl. Acad. Sci, USA 91, 2216–2220) [e.g. Expand High Fidelity PCR System (Taq+Pwo), (Boehringer Mannheim. Indianapolis, Ind.) OR GeneAmp XL PCR kit (Tth+Vent), (Roche Molecular Systems, Inc., Branchburg, N.J.), Advantage-2, (CloneTech).

Oligo-dT was used for reverse transcription of viral RNA into first strand cDNA. Envelope PCR primers, forward primer Xho/Pin and reverse primer Mlu/Xba (Table 3) were used to amplify the patient-derived segments. These primers are designed to amplify the ~2.5 kB envelope gene encoding the gp160 envelope polyprotein, while introducing Xho I and Pin AI recognition sites at the 5' end of the PCR amplification product, and Mlu I and Xba I sites at the 3' end of the PCR amplification product.

Patient derived segments (2.5 kB envelope sequence amplification product) were inserted into HIV-1 envelope expression vectors using restriction endonuclease digestion, DNA ligation and bacterial transformation methods as described in U.S. Pat. No. 5,837,464 (International Publication Number WO 97/27319), with minor adaptations. The ~2.5 kB amplification product was digested with either Xho I or Pin AI at the 5' end and either Mlu I or Xba I at the 3' end. The resulting digestion products were ligated, using DNA ligase, into the 5' Xho I/Pin AI and 3' Mlu I/Xba I sites of modified pCXAS or pCXAS expression vectors. The construction of the pCXAS and pCXAT vectors was described in U.S. Pat. No. 5,837,464. Modified pCXAS and pCXAT vectors contain a Pin AI restriction site in addition to the Xho I, MluI and Xba I restriction sites that exist in pCXAS and pCXAT. The Pin AI site was introduced between the Xho I and Mlu I sites by site directed mutagenesis, such that the four sites are located 5' to 3' in the following order; Xho I, Pin AI, Mlu I and Xba I. In a preferred embodiment, the 2.5 kB amplification products were digested with Pin AI and Mlu I and ligated into the 5' Pin AI site and the 3' Mlu I site of the modified pCXAS expression vector. Ligation reaction products were used to transform E. coli. Following a 24–36 h incubation period at 30–37° C., the expression vector plasmid DNA was purified from the E. coli cultures. To ensure that expression vector preparations adequately represents the HIV quasi-species present in the serum of a given patient, many (>100) independent E. coli transformants were pooled and used for the preparations of pHIVenv plasmid DNA. Vectors that are assembled in this manner for the purposes of expressing patient virus derived envelope proteins are collectively referred to as pHIVenv (FIGS. 1 and 3).

The genomic HIV expression vectors pHIVluc and pHIVluc@U3 are designed to transcribe HIV genomic RNA and subgenomic mRNAs and to express all HIV proteins except the envelope polyprotein (FIG. 1B). In these vectors, a portion of the envelope gene has been deleted to accommodate a functional indicator gene cassette, in this case, "Firefly Luciferase" that is used to monitor the ability of the virus to replicate in the presence or absence of anti-viral drugs. In pHIVluc@U3, a portion of the 3' U3 region has been deleted to prevent transcription of viral RNAs from the 5' LTR in infected cells.

Susceptibility assays for HIV-1 entry inhibitors were performed using packaging host cells consisting of the human embryonic kidney cell line 293 (Cell Culture Facility, UC San Francisco, SF, Calif.) and target host cells consisting of a human osteosarcoma (HOS) cell line expressing CD4 (HT4) plus CCR5, and CXCR4, or astrocytoma (U-87) cell lines expressing either CD4 and CCR5 or CD4 and CXCR4.

Drug susceptibility testing was performed using pHIVenv and pHIVluc or pHIVluc U3. Pseudotyped HIV particles containing envelope proteins encoded by the patient derived segment were produced by transfecting a packaging host cell (HEK 293) with resistance test vector DNA. Virus particles were collected (~48 h) after transfection and are used to infect target cells (HT4/CCR5/CXCR4, or U-87/CD4/CXCR4, or U-87/CD4/CCR5) that express HIV receptors (i.e. CD4) and co-receptors (i.e. CXCR4, CCR5). After infection (~72 h) the target cells are lysed and luciferase activity is measured. HIV must complete one round of replication to successfully infect the target host cell and produce luciferase activity. The amount of luciferase activity detected in the infected cells is used as a direct measure of "infectivity" (FIGS. 1 and 2). If for any reason (e.g. lack of the appropriate receptor or co-receptor, inhibitory drug activity, neutralizing antibody binding), the virus is unable to enter the target cell, luciferase activity is diminished. Drug susceptibility is assessed by comparing the infectivity in the absence of drug to infectivity in the presence of drug. Relative drug susceptibility can be quantified by comparing the susceptibility of the "test" virus to the susceptibility of a well-characterized reference virus (wildtype) derived from a molecular clone of HIV-1, for example NL4-3 or HXB2.

Packaging host cells were seeded in 10-cm-diameter dishes and were transfected one day after plating with pHIVenv and pHIVluc or pHIVlucÄU3. Transfections were performed using a calcium-phosphate co-precipitation procedure. The cell culture media containing the DNA precipitate was replaced with fresh medium, from one to 24 hours, after transfection. Cell culture media containing viral particles was typically harvested 2 days after transfection and was passed through a 0.45-mm filter. Before infection, target cells were plated in cell culture media. Entry inhibitor drugs were typically added to target cells at the time of infection (one day prior to infection on occasion). Typically, 3 days after infection target cells were assayed for luciferase activity using the Steady-Glo reagent (Promega) and a luminometer.

In one embodiment, the susceptibility to a fusion inhibitor drug (T-20, also referred to as DP178; Trimeris, Research Triangle Park, N.C.) was demonstrated (FIG. 6). Target cells (HT4/CCR5/CXCR4) expressing CD4, CCR5 and CXCR4 were infected in the absence of T-20 and over a wide range of T-20 concentrations (x-axis $\log_{10}$ scale). The percent inhibition of viral replication (y-axis) was determined by comparing the amount of luciferase produced in infected cells in the presence of T-20 to the amount of luciferase produced in the absence of T-20. R5 tropic (JRCSF, 91US005.11), X4 tropic (NL4-3, 92HT599.24) and dual tropic (92HT593.1) viruses were tested. Drug susceptibility is quantified by determining the concentration of T-20 required to inhibit viral replication by 50% ($IC_{50}$, shown as vertical dashed lines in FIG. 6). Viruses with lower $IC_{50}$ values are more susceptible to T-20 than viruses with higher $IC_{50}$ values.

In still further embodiments, susceptibility to a wide variety of entry inhibitors can be measured. These inhibitors include, but are not limited to, the drugs and compound listed in Table 4 (anti-HIV drug table).

In a second embodiment, susceptibility to a CCR5 inhibitor belonging to the 4-(piperidin-1-yl) butane class of compounds (Dorn, C. P. et al., (2001), Finke, P. E. et al., (2001); Merck, West Point, Pa.) is demonstrated. Target cells (U-87/CD4/CCR5) expressing CD4 and CCR5 (R5 cells) were infected in the absence of the CCR5 inhibitor and over a wide range of CCR5 inhibitor concentrations (x-axis $\log_{10}$ scale). The percent inhibition of viral replication (y-axis) was determined by comparing the amount of luciferase produced in infected cells in the presence of CCR5 inhibitor to the amount of luciferase produced in the absence of CCR5 inhibitor. R5 tropic (JRCSF), X4 tropic (NL4-3) and dual tropic viruses (92HT593.1) were tested. Drug susceptibility was quantified by determining the concentration of CCR5 inhibitor required to viral replication by 50% ($IC_{50}$, shown as vertical dashed lines in FIG. 8). Viruses with lower $IC_{50}$ values are more susceptible to the CCR5 inhibitor than viruses with higher $IC_{50}$ values. The X4 tropic virus did not infect the U-87/CD4/CCR5 target cells.

In a third embodiment, susceptibility to a CXCR4 inhibitor (AMD3100; AnorMED) was demonstrated. Target cells (U87/CD4/CXCR4) expressing CD4 and CXCR4 were infected in the absence of the CXCR4 inhibitor and over a wide range of CXCR4 inhibitor concentrations (x-axis $\log_{10}$, scale). The percent inhibition of viral replication (y-axis) was determined by comparing the amount of luciferase produced in infected cells in the presence of CXCR4 inhibitor to the amount of luciferase produced in the absence of CXCR4 inhibitor. R5 tropic (JRCSF), X4 tropic (NL4-3) and dual tropic (92HT593.1) viruses were tested. Drug susceptibility is quantified by determining the concentration of CXCR4 inhibitor required to inhibit viral replication by 50% ($IC_{50}$, shown as vertical dashed lines in FIG. 9). Viruses with lower $IC_{50}$ values are more susceptible to the CCR5 inhibitor than viruses with higher $IC_{50}$ values. The R5 tropic virus did not infect the U-87/CD4/CXCR4 target cells.

Susceptibility to a CD4 inhibitor (e.g. murine monoclonal antibody 5A8; Tanox, Houston, Tex.) can be measured. Target cells (e.g. HT4/CCR5/CXCR4, U-87/CD4/CXCR4, or U-87/CD4/CCR5) expressing CD4 and one or both co-receptors can be infected in the absence of the CD4 inhibitor drug and over a wide range of CD4 inhibitor drug concentrations (x-axis $\log_{10}$ scale). The percent inhibition of viral replication (y-axis) can be determined by comparing the amount of luciferase produced in infected cells in the presence of CD4 inhibitor to the amount of luciferase produced in the absence of CD4 inhibitor. R5 tropic (e.g. JRCSF), X4 tropic (e.g. NL4-3) and dual tropic (e.g. 92HT593.1) viruses can be tested. Drug susceptibility can be quantified by determining the concentration of CD4 inhibitor required to inhibit viral replication by 50% ($IC_{50}$). Viruses with lower $IC_{50}$ values are more susceptible to the CD4 inhibitor than viruses with higher $IC_{50}$ values.

EXAMPLE 2

Discovery, Optimization and Characterization of New and Novel Inhibitors of Virus Entry.

In one embodiment, the virus entry assay can be used to identify new compounds/chemical entities that inhibit virus entry. Target cells (e.g. HT4/CCR5/CXCR4, U-87/CD4/CXCR4, or U-87/CD4/CCR5) expressing CD4 and one or both co-receptors can be infected in the presence of individual members of large chemical libraries (high throughput screening, HTS). The ability of a compound to inhibit viral replication (a "hit") can be determined by comparing the amount of luciferase produced in infected target cells in the presence of a specific compound to the amount of luciferase produced in the absence of the compound.

In a further embodiment, the virus entry assay can be used to optimize the antiviral activity of lead compounds identified by HTS. Chemical modified derivatives of lead compounds can be tested to identify specific derivatives that have enhanced virus entry inhibitory activity. Target cells (e.g. HT4/CCR5/CXCR4, U-87/CD4/CXCR4, or U-87/CD4/CCR5) expressing CD4 and one or both co-receptors can be infected in the absence of the inhibitor candidate and over a wide range of inhibitor candidate concentrations (x-axis $\log_{10}$ scale). The percent inhibition of viral replication (y-axis) can be determined by comparing the amount of luciferase produced in infected cells in the presence of the candidate inhibitor to the amount of luciferase produced in the absence of candidate inhibitor. Drug susceptibility can be quantified by determining the concentration of inhibitor candidate required to inhibit viral replication by 50% ($IC_{50}$). Derivatized compounds with lower $IC_{50}$ values are more potent inhibitors of virus entry (have greater antiviral activity) than derivatives with higher $IC_{50}$ values.

In yet a further embodiment, the virus entry assay can be used to characterize the mechanism of action of new virus entry inhibitor drug candidates, and the antiviral activity against a spectrum of viruses that may differ in susceptibility. Target cells (e.g. HT4/CCR5/CXCR4, U-87/CD4/CXCR4, or U-87/CD4/CCR5) expressing CD4 and one or both co-receptors can be infected in the absence of the new entry inhibitor drug candidate and over a wide range of entry inhibitor drug concentrations (x-axis $\log_{10}$, scale). The percent inhibition of viral replication (y-axis) can be determined by comparing the amount of luciferase produced in infected cells in the presence of new entry inhibitor to the amount of luciferase produced in the absence of the new entry inhibitor. R5 tropic (e.g. JRCSF), X4 tropic (e.g. NL4-3) and dual tropic (e.g. 92HT593.1) viruses can be tested. Drug susceptibility can be quantified by determining the concentration of CD4 inhibitor required to inhibit viral replication by 50% ($IC_{50}$).

To determine whether the new entry inhibitor acts by blocking the CCR5 or CXCR4 co-receptors, the R5 tropic viruses are tested against the new inhibitor in U-87/CD4/CCR5 cells and X4 tropic viruses are tested against the new inhibitor using U-87/CD4/CXCR4 cells. Inhibition of R5 virus infection is indicative of CCR5 co-receptor antagonism and conversely, inhibition of X4 virus infection is indicative of CXCR4 co-receptor antagonism. Inhibition of R5 and X4 virus infection may be indicative of either CD4 antagonism or the inhibition of membrane fusion.

To characterize the activity of a new inhibitor against viruses that exhibit resistance, or have reduced susceptibility, to other virus entry inhibitors of the same class, or different class, selected panels of drug resistant viruses can be tested in the virus entry assay using the new entry inhibitor drug. The panel may include viruses with varying levels of susceptibility to CCR5 inhibitors, CXCR4 inhibitors, CD4 inhibitors, and membrane fusion inhibitors. The panel may include viruses with one or more specific mutations that are associated with reduced susceptibility/resistance to one or more entry inhibitors.

EXAMPLE 3

Identifying Envelope Amino Acid Substitutions/mutations that Alter Susceptibility to Virus Entry Inhibitors.

This example provides a means and method for identifying mutations in HIV-1 envelope that confer reduced susceptibility/resistance to virus entry inhibitors. This example also provides a means and method for quantifying the degree of reduced susceptibility to entry inhibitors conferred by specific envelope mutations.

Envelope sequences derived from patient samples, or individual clones derived from patient samples, or envelope sequences engineered by site directed mutagenesis to contain specific mutations, are tested in the entry assay to quantify drug susceptibility based on a well-characterized reference standard (e.g. NL4-3, HXB2).

In one embodiment, susceptibility to longitudinal patient samples (viruses collected from the same patient at different timepoints) is evaluated. For example, susceptibility to entry inhibitors is measured prior to initiating therapy, before or after changes in drug treatment, or before or after changes in virologic (RNA copy number), immunologic (CD4 T-cells), or clinical (opportunistic infection) markers of disease progression.

Genotypic Analysis of Patient HIV Samples

Envelope sequences representing patient sample pools, or clones derived from patient pools, can be analyzed by any broadly available DNA sequencing methods. In one embodiment of the invention, patient HIV sample sequences are determined using viral RNA purification, RT/PCR and dideoxynucleotide chain terminator sequencing chemistry and capillary gel electrophoresis (Applied Biosystems, Foster City, Calif.). Envelope sequences of patient virus pools or clones are compared to reference sequences, other patient samples, or to a sample obtained from the same patient prior to initiation of therapy, if available. The genotype is examined for sequences that are different from the reference or pre-treatment sequence and correlated to differences in entry inhibitor susceptibility.

Entry Inhibitor Susceptibility of Site Directed Mutants

Genotypic changes that correlate with changes in fitness are evaluated by constructing envelope expression vectors (pHIVenv) containing the specific mutation on a defined, drug susceptible, genetic background (e.g. NL4-3 reference strain). Mutations may be incorporated alone and/or in combination with other mutations that are thought to modulate the entry inhibitor susceptibility. Envelope mutations are introduced into pHIVenv vectors using any of the broadly available methods for site-directed mutagenesis. In one embodiment of this invention the mega-primer PCR method for site-directed mutagenesis is used (Sarkar, G. and Summer, S. S., 1990). A pHIVenv vector containing a specific envelope mutation or group of mutations are tested using the virus entry assay described in Example 1. Drug susceptibility of the virus containing envelope mutations is compared to the drug susceptibility of a genetically defined drug susceptible virus that lacks the specific mutations under evaluation. Observed changes in entry inhibitor susceptibility are attributed to the specific mutations introduced into the pHIVenv vector.

In one embodiment of the invention, reduced susceptibility to the fusion inhibitor T-20 conferred by specific drug resistance mutations in the gp41 envelope protein is demonstrated (FIG. 7). Cells expressing CD4, CCR5 and CXCR4 were infected in the absence of T-20 and over a wide range of T-20 concentrations (x-axis log 10 scale). The percent inhibition of viral replication (y-axis) was determined by comparing the amount of luciferase produced in infected cells in the presence of T-20 to the amount of luciferase produced in the absence of T-20. Isogenic viruses containing one or two specific mutations in the gp41 transmembrane envelope protein were tested (highlighted in red in the figure legend; Rimsky et al., J. Virol. 72: 986–993). Drug susceptibility is quantified by determining the concentration of T-20 required to inhibit viral replication by 50% ($IC_{10}$, shown as vertical dashed lines). Viruses with lower $IC_{50}$ values are more susceptible to T-20 than viruses with higher $IC_{50}$ values.

In one embodiment, drug resistance mutations were introduced into well-characterized X4 tropic (NL4-3) and R5 tropic (JRCSF) viruses. T20 susceptibility was measured using the virus entry assay (FIG. 7). The fold change (FC) in T-20 susceptibility for each virus was determined by dividing the IC50 of the test virus by the IC50 of the HXB2 strain of HIV-1. T-20 sensitivity of similar mutant viruses has been reported in the scientific literature (Rimsky et al.,). In this embodiment, viruses with one mutation within the GIV motif of gp41 (DIV, GIM, SIV) were less susceptible to T20 than the wildtype virus (GIV) (Table 6). Viruses with two mutations within the GIV motif (DIM, SIM, DTV) were less susceptible to T20 than viruses with one, or no mutations in the GIV motif (Table 6).

In another embodiment, mutations that may confer reduced (or increased) susceptibility to the entry inhibitor are identified by sequencing the envelope genes of the sensitive and resistant viruses. The deduced amino acid sequences of the sensitive and resistant viruses are compared to identify candidate drug resistance mutations. The ability of a specific mutation to confer altered drug susceptibility is confirmed or disproved by introducing the mutation into a drug sensitive virus and measuring the susceptibility of the mutant virus in the virus entry assay. In the example represented here, a short stretch of amino acid sequences within the first heptad repeat (HR-1) of the HIV-1 gp41 transmembrane envelope protein is aligned for viruses exhibiting different T-20 susceptibilities (Table 6). Highlighted amino acids represent mutations known to confer reduced susceptibility to T-20.

Similar phenotypic and genotypic analyses can be used to identify envelope amino acid sequences that (a) alter/influence susceptibility to CCR5 or CXCR4 inhibitors, (b) specify X4, R5 and dual tropism, and (c) elicit neutralizing antibodies.

In one embodiment, reduced susceptibility to co-receptor (CCR5, CXCR4) inhibitors conferred by specific envelope amino acid sequences/mutations is demonstrated.

In a further embodiment, reduced susceptibility to receptor (CD4) inhibitors conferred by specific envelope amino acid sequences/mutations is demonstrated.

EXAMPLE 4

Determining HIV-1 Co-receptor and Receptor Tropism

This example provides a means and method for determining HIV-1 co-receptor tropism. This example also provides a means and method for determining HIV-1 receptor tropism.

In one embodiment, viruses that use the CCR5 co-receptor are identified. In a related embodiment, viruses that use the CXCR4 co-receptor are identified. In a further related embodiment, viruses that use CCR5 and CXCR4 are identified.

In a further related embodiment, viruses that use co-receptors other than CCR5 or CXCR4 are identified.

In another embodiment, viruses that use the CD4 receptor are identified. In a related embodiment, viruses that use CD8 are identified. In a further related embodiment, viruses that do not require CD4 or CD8 to infect cells are identified.

In this embodiment, the assay is performed using two cell lines. One cell line expresses CD4 plus CCR5 (U-87/CD4/CCR5), also referred to as R5 cells in this application. The other cell line expresses CD4 and CXCR4 (U87/CD4/CXCR4) also referred to as X4 cells in this application. The virus entry assay is performed by infecting individual cell cultures with recombinant virus stocks derived from cells transfected with pHIVenv and pHIV luc or pHIVlucDU3 vectors. pHIVenv vectors contain patient virus derived sequences and express HIV-1 envelope proteins (gp120SU, gp41TM). In this embodiment viruses are evaluated in using R5 and X4 target cells cultured in 96 well plates (FIG. 3A). Typically, R5 and X4 cells are plated one day prior to infection. Infection with each virus stock is performed in the absence of drug (no drug), in the presence of inhibitory concentrations of a drug that preferentially inhibits R5 tropic viruses (CCR inhibitor, e.g. a piperidin 1yl butane compound), and in the presence of inhibitory concentrations of a drug that preferentially inhibits X4 tropic viruses (CXCR4 inhibitor, e.g. AMD3100). Co-receptor tropism is assessed by comparing the amount of luciferase activity produced in each cell type, both in the presence and absence of drug. In this embodiment, the results of the assay are interpreted by comparing the ability of each virus to preferentially infect (produce luciferase activity) R5 cells or X4 cells, or both X4 and R5 cells if the virus is dual tropic. The ability of the CCR5 or CXCR4 inhibitor to specifically block infection (inhibit luciferase activity) is also evaluated (FIG. 3B). In this embodiment, X4 tropic viruses infect X4 cells but not R5 cells and infection of X4 cells is blocked by the the CXCR4 inhibitor (AMD3100). In this embodiment, R5 tropic viruses infect R5 cells but not X4 cells and infection of R5 cells is blocked by the CCR5 inhibitor (piperidin-1yl butane compound). In this embodiment, dual tropic, or mixtures of X4 and R5 tropic viruses, infect both X4 and R5 cells and infection of R5 cells is blocked by the CCR5 inhibitor and infection of X4 cells is blocked by the CXCR4 inhibitor. In this embodiment, non-viable viruses do not replicate in either X4 or R5 cells (luciferase activity is not produced).

In another embodiment, the assay is performed using three or more cell lines. One cell line expresses CD4 plus CCR5 (U-87/CD4/CCR5), also referred to as R5 cells in this application. The other cell line expresses CD4 and CXCR4 (U-87/CD4/CXCR4) also referred to as X4 cells in this application. Additional cell lines express CD4 plus other candidate HIV-1 co-receptors, including, but not limited to, BONZO, BOB, etc. See Table 1. These additional cell lines express other candidate co-receptors, but do not express CCR5 or CXCR4. The virus entry assay is performed by infecting individual cell cultures with recombinant virus stocks derived from cells transfected with pHIVenv and pHIV luc or pHIVlucDU3 vectors. pHIVenv vectors contain patient virus derived sequences and express HIV-1 envelope proteins (gp120SU, gp41TM). In this embodiment viruses are evaluated in using cells cultured in 96 well plates. Infection with each virus stock is performed in R5 cells, X4 cells and the cell lines expressing CD4 plus the candidate co-receptors. Co-receptor tropism is assessed by comparing the amount of luciferase activity produced in each cell type. In this embodiment, the results of the assay are interpreted by comparing the ability of each virus to preferentially infect (produce luciferase activity) R5 cells or X4 cells, or the cell line that expresses the candidate co-receptor. In this embodiment, X4 tropic viruses infect X4 cells but not R5 cells. In this embodiment, R5 tropic viruses infect R5 cells but not X4 cells. In this embodiment dual tropic, or mixtures of X4 and R5 tropic viruses, infect both X4 and R5 cells. In this embodiment, the infection of cell lines expressing alternative candidate co-receptors (neither CCR5 or CXCR4) is attributed to tropism for the alternative co-receptor. In this embodiment, non-viable viruses do not replicate in either X4 or R5 cells.

In another embodiment, the assay is performed using four cell lines. One cell line expresses CD4 plus CCR5 (U-87/CD4/CCR5), also referred to as R5 cells in this application. A second other cell line expresses CD4 and CXCR4 (U-87/CD4/CXCR4) also referred to as X4 cells in this application. A third cell line expresses CD8 plus CCR5 (U-87/CD8/CCR5), also referred to as CD8/R5 cells in this application. A fourth cell line expresses CD8 and CXCR4 (U-87/CD8/CXCR4) also referred to as CD8/X4 cells in this application. The virus entry assay is performed by infecting individual cell cultures with recombinant virus stocks derived from cells transfected with pHIVenv and pHIV luc or pHIVlucDU3 vectors. pHIVenv vectors contain patient virus derived sequences and express HIV-1 envelope proteins (gp120SU, gp41TM). In this embodiment viruses are evaluated in using cells cultured in 96 well plates. Infection with each virus stock is performed in R5 cells, X4 cells, CD8/R5 cells and CD8/X4 cells. Co-receptor tropism is assessed by comparing the amount of luciferase activity produced in each cell type. In this embodiment, the results of the assay are interpreted by comparing the ability of each virus to preferentially infect (produce luciferase activity) R5 cells, X4 cells, CD8/R5 cells, or CD8/X4 cells. In this embodiment, CD4 tropic viruses infect X4 cells and/or R5 cells. In this embodiment, CD8 tropic viruses infect CD8/R5 cells and/or CD8/X4 cells. In this embodiment, dual tropic (CD4 and CD8 receptor use) viruses infect X4 cells and/or R5 cells plus CD8/X4 and/or CD8/R5 cells. In this embodiment, the infection of cell lines expressing CD8 but not CD4 is attributed to CD8 receptor tropism. In this embodiment, non-viable viruses do not replicate in either X4 or R5 cells.

In a further related embodiment, the assay is performed using two cell lines. One cell line expresses CD4 plus CCR5 and CXCR4 (HT4/CCR5/CXCR4). A second cell line expresses CD8 plus CCR5 and CXCR4 (HOS/CD8/CCR5/CXCR4). The virus entry assay is performed by infecting individual cell cultures with recombinant virus stocks derived from cells transfected with pHIVenv and PHIV luc or pHIVlucDU3 vectors. pHIVenv vectors contain patient virus derived sequences and express HIV-1 envelope proteins (gp120SU, gp41TM). In this embodiment viruses are evaluated in using cells cultured in 96 well plates. Infection with each virus stock is performed in HT4/CCR5/CXCR4 cells and HOS/CD8/CCR5/CXCR4 cells. Co-receptor tropism is assessed by comparing the amount of luciferase activity produced in each cell type. In this embodiment, the results of the assay are interpreted by comparing the ability of each virus to preferentially infect (produce luciferase activity) HT4/CCR5/CXCR4 cells or HOS/CD8/CCR5/CXCR4 cells. In this embodiment, CD4 tropic viruses infect HT4/CCR5/CXCR4 cells, but not HOS/CD8/CCR5/CXCR4 cells. In this embodiment, CD8 tropic viruses infect HOS/CD8/CCR5/CXCR4 cells but not HT$/CCR5/CXCR4 cells. In this embodiment, dual tropic (CD4 and CD8 receptor use) viruses infect both HT4/CCR5/CXCR4 cells and HOS/CD8/CCR5/CXCR4 cells. In this embodiment, the infection of cell lines expressing CD8 but not CD4 is attributed to CD8 receptor tropism. In this embodiment, non-viable viruses do not replicate in either X4 or R5 cells.

In another embodiment, the assay is performed using two cell lines. One cell line expresses CD4 plus CCR5 and CXCR4 (HT4/CCR5/CXCR4). A second cell line expresses CCR5 and CXCR4 but not CD4 or CD8 (HOS/CCR5/CXCR4). The virus entry assay is performed by infecting individual cell cultures with recombinant virus stocks derived from cells transfected with pHIVenv and PHIV luc or pHIVlucDU3 vectors. pHIVenv vectors contain patient virus derived sequences and express HIV-1 envelope proteins (gp120SU, gp41TM). In this embodiment viruses are evaluated in using cells cultured in 96 well plates. Infection with each virus stock is performed in HT4/CCR5/CXCR4 cells and HOS/CCR5/CXCR4 cells. CD4 and CD8 independent infection is assessed by comparing the amount of luciferase activity produced in each cell type. In this embodiment, the results of the assay are interpreted by comparing the ability of each virus to preferentially infect (produce luciferase activity) HT4/CCR5/CXCR4 cells or HOS/CCR5/CXCR4 cells. In this embodiment, CD4 dependent viruses infect HT4/CCR5/CXCR4 cells, but not HOS/CCR5/CXCR4 cells. In this embodiment, CD4 independent viruses infect both HOS/CCR5/CXCR4 cells and HT4/CCR5/CXCR4 cells. In this embodiment, the infection of cell lines that lack CD4 expression is attributed to CD4 independent infection. In this embodiment, non-viable viruses do not replicate in either X4 or R5 cells.

EXAMPLE 5

Identifying HIV-1 Envelope Amino Acid Substitutions/Mutations that Alter Co-receptor and Receptor Tropism This example provides a means and method for identifying HIV-1 envelope amino acid sequences that specify, or alter, co-receptor tropism (X4 vs. R5 vs. dual X4/R5). This example also provides a means and method for identifying HIV-1 envelope amino acid sequences that specify co-receptor usage other than CXCR4 or CCR5. The example also provides a means and method for identifying HIV-1 envelope sequences that specific, or receptor tropism (CD4 vs. CD8).

Envelope sequences derived from patient samples, or individual clones derived from patient samples, or envelope sequences engineered by site directed mutagenesis to contain specific mutations, are tested in the entry assay to determine co-receptor tropism as described in Example 4.

In one embodiment, co-receptor tropism of longitudinal patient samples (viruses collected from the same patient at different timepoints) is evaluated. For example, co-receptor tropism is evaluated prior to initiating therapy, before or after changes in drug treatment, or before or after changes in virologic (RNA copy number), immunologic (CD4 T-cells), or clinical (opportunistic infection) markers of disease progression.

In another embodiment, co-receptor tropism is evaluated for samples collected from a large number of different patients. In a further embodiment, co-receptor tropism is evaluated for samples collected from a large number of patients representing different virus and patient populations. Such patient populations may include, but are not limited to, newly infected patients, chronically infected patients, patients with advanced disease, and patients undergoing antiretroviral therapy or immuno-therapy. Such virus populations may include, but are not limited to, viruses with distinct genetic characteristics (clade A, B, C, D, E, F, G), viruses susceptible to antiretroviral drugs, viruses with reduced susceptibility/resistance to antiretroviral drugs.

Genotypic Analysis of Patient HIV Samples

Envelope sequences representing patient sample pools, or clones derived from patient pools, can be analyzed by any broadly available DNA sequencing methods. In one embodiment of the invention, patient HIV sample sequences are determined using viral RNA purification, RT/PCR and dideoxynucleotide chain terminator sequencing chemistry and capillary gel electrophoresis (Applied Biosystems, Foster City, Calif.). Envelope sequences of patient virus pools or clones are compared to reference sequences, other patient samples, or to a sample obtained from the same patient prior to initiation of therapy, if available. The genotype is examined for sequences that are different from the reference or pre-treatment sequence and correlated to differences in entry inhibitor susceptibility.

Co-receptor and Receptor Tropism of Genetically Characterized Viruses

Envelope amino acid sequences that correlate co-receptor tropism are evaluated by constructing envelope expression vectors (pHIVenv) containing a specific mutation on a defined genetic background (e.g. NL4-3 for X4 tropism, JRCSF for R5 tropism). Mutations may be incorporated alone and/or in combination with other mutations that are thought to modulate co-receptor usage. Envelope mutations are introduced into pHIVenv vectors using any of the broadly available methods for site-directed mutagenesis. In one embodiment of this invention the mega-primer PCR method for site-directed mutagenesis is used (Sarkar, G. and Summer, S. S., 1990). A pHIVenv vector containing a specific envelope mutation or group of mutations are tested using the virus entry assay described in Example 1. Co-receptor tropism of the virus containing envelope mutations is compared to the co-receptor tropism of a genetically defined virus that lacks the specific mutations under evaluation. The ability of a specific mutation to confer altered co-receptor tropism is confirmed or disproved by introducing the mutation into well-characterized reference virus and evaluating the co-receptor tropism of the mutant virus in the virus entry assay as described in Example 4. Observed changes in co-receptor tropism are attributed to the specific mutations introduced into the pHIVenv vector.

In one embodiment of the invention, genetic determinants of R5 tropism are identified by evaluating amino acid sequences within the V3 loop of the gp120 surface envelope protein. The amino acid sequences under evaluation are identified by comparing the amino acid sequences of large numbers of X4tropic and R5 tropic viruses. Consistent differences between the X4 and R5 viruses are selected for evaluation. Isogenic viruses based on an well-characterized X4 parental clone (e.g NL4-3, HXB2) containing specific "R5 candidate" mutations in the V3 loop of the gp120 envelope protein are constructed by site directed mutagenesis and tested for co-receptor tropism as described in Example 4. Cells expressing CD4 plus CCR5 (e.g. U-87/CD4/CCR5) or CD4 plus CXCR4 (U-87/CD4/CXCR4) are infected in the absence of an R5 (peperidin-1yl butane compound) and X4 (AMD3100) inhibitor and in the presence of inhibitory concentrations of R5 and X4 drug concentrations. Amino acid substitutions that change the X4 tropic virus to an R5 tropic virus are characterized as genetic determinants of R5 tropism.

In a related embodiment of the invention, genetic determinants of X4 tropism are identified by evaluating amino acid sequences within the V3 loop of the gp120 surface envelope protein. The amino acid sequences under evaluation are identified by comparing the amino acid sequences of large numbers of X4 tropic and R5 tropic viruses. Consistent differences between the X4 and R5 viruses are selected for evaluation. Isogenic viruses based on an well-characterized R5 parental clone (e.g JRCSF) containing specific "X4 candidate" mutations in the V3 loop of the gp120 envelope protein are constructed by site directed mutagenesis and tested for co-receptor tropism as described in Example 4. Cells expressing CD4 plus CCR5 (e.g. U-87/CD4/CCR5) or CD4 plus CXCR4 (U-87/CD4/CXCR4) are infected in the absence of an R5 (peperidin-1yl butane compound) and X4 (AMD3100) inhibitor and in the presence of inhibitory concentrations of R5 and X4 drug concentrations. Amino acid substitutions that change the X4 tropic virus to an R5 tropic virus are characterized as genetic determinants of R5 tropism.

In a related embodiments of the invention, genetic determinants of X4 or R5 tropism are identified by evaluating amino acid sequences within the entire gp120 surface envelope protein.

In a related embodiment of the invention, genetic determinants of X4 or R5 tropism are identified by evaluating amino acid sequences within the gp41 transmembrane envelope protein.

In a related embodiment of the invention, genetic determinants that specify the use of co-receptors other than CCR5 and CXCR4 are identified by evaluating amino acid sequences within the V3 loop of the gp120 surface envelope protein. The amino acid sequences under evaluation are identified by comparing the amino acid sequences of viruses that are able to replicate on cells that do not express CXCR4 or CCR5, but do express other candidate co-receptors. Consistent differences in amino acid sequences between these non-X4, non R5 viruses and the X4 and R5 viruses are selected for evaluation. Isogenic viruses based on an well-characterized X4 (e.g. NL4-3) or R5 (e.g. JRCSF) parental clone containing specific "non-X4, non-R5 candidate" mutations in the V3 loop of the gp120 envelope protein are constructed by site directed mutagenesis and tested for co-receptor tropism as described in Example 4. Cells expressing CD4 plus CCR5 (e.g. U-87/CD4/CCR5), CD4 plus CXCR4 (U-87/CD4/CXCR4), and CD4 plus other candidate co-receptors (U-87/CD4/X) are infected in the absence of an R5 (peperidin-1yl butane compound) and X4 (AMD3100) inhibitor and in the presence of inhibitory concentrations of R5 and X4 drug concentrations. Amino acid substitutions that confers tropism for a non-X4, non-R5 co-receptor are characterized as genetic determinants of tropism for the specific co-receptor.

In a related embodiments of the invention, genetic determinants of tropism for other co-receptors are identified by evaluating amino acid sequences within the entire gp120 surface envelope protein.

In a related embodiment of the invention, genetic determinants of tropism for other co-receptors are identified by evaluating amino acid sequences within the gp41 transmembrane envelope protein.

In another embodiment of the invention, genetic determinants that specify the use of CD8 (in addition to, or instead of CD4) as a receptor for HIV-1 are identified by evaluating amino acid sequences within the V3 loop of the gp120 surface envelope protein. The amino acid sequences under evaluation are identified by comparing the amino acid sequences of viruses that are able to replicate in cells that do not express CD4, but do express CD8. Consistent differences in amino acid sequences between these CD4 tropic viruses and CD8 tropic viruses are selected for evaluation. Isogenic viruses based on an well-characterized CD4 tropic (e.g. NL4-3, JRCSF) parental clones containing specific "CD8 candidate" mutations in the V3 loop of the gp120 envelope protein are constructed by site directed mutagenesis and tested for CD8 receptor tropism as described in Example 4. Cells expressing CD4 plus CCR5 (e.g. U-87/CD4/CCR5), CD4 plus CXCR4 (U-87/CD4/CXCR4), CD8 plus CCR5 (e.g. U-87/CD8/CCR5), CD8 plus CXCR4 (U-87/CD8/CXCR4) are infected. Amino acid substitutions that enable replication in cells that express CD8 but not CD4 are characterized as genetic determinants of CD8 tropism.

In a related embodiments of the invention, genetic determinants of CD8 tropism are identified by evaluating amino acid sequences within the entire gp120 surface envelope protein.

In a related embodiment of the invention, genetic determinants of CD8 tropism are identified by evaluating amino acid sequences within the gp41 transmembrane envelope protein.

EXAMPLE 6

Measuring HIV-1 Antibody Neutralization

This example provides a means and method for evaluating antibody mediated neutralization of HIV-1, also referred to as virus neutralization in this application. This example also provides a means and method for evaluating the virus neutralization activity of antibodies within HIV-1 infected patients. This example also provides a means and method for evaluating the virus neutralizing activity of antibodies within individuals or animals vaccinated with therapeutic vaccines and vaccine candidates. This example also provides a means and method for evaluating the virus neutralizing activity of antibodies within individuals or animals vaccinated with protective (preventative or prophylactic) vaccine and vaccine candidates. This example also provides a means and method for evaluating the virus neutralizing activity or preparations of specific monoclonal or polyclonal antibodies.

Envelope sequences derived from patient samples, or individual clones derived from patient samples, or envelope sequences engineered by site directed mutagenesis to contain specific mutations, are tested in the entry assay to evaluate antibody mediated neutralization.

In one embodiment, antibody mediated neutralization is evaluated in longitudinal patient samples (viruses collected from the same patient at different time points) is evaluated. For example, virus neutralization is evaluated prior to vaccination, during a course of vaccination, and at incremental time points after the course of vaccination is completed. In a related embodiment, the sera of animals including, but not limited to, mice, rats, rabbits, pigs, and cattle, are evaluated prior to inoculation with candidate vaccines, during a course of repeated inoculation, and at incremental time points after the course of inoculation is completed. In one embodiment, virus neutralization is evaluated for preventative vaccines and vaccine candidates. In another embodiment, virus neutralization is evaluated for therapeutic vaccines.

In another embodiment, virus neutralization is evaluated for samples collected from a large number of different patients.

In a further embodiment, virus neutralization is evaluated for samples collected from a large number of patients representing different patient populations and different virus populations. "Patient populations" may include, but are not limited to, newly infected patients, chronically infected patients, patients with advanced HIV/AIDS disease, patients with rapid disease progression, patients with slow disease progression (typically referred to as long term non-progressors), patients undergoing antiretroviral therapy or immunotherapy (e.g. interleukin-2, or other cytokines), vaccinated and unvaccinated individuals. "Virus populations" may include, but are not limited to, viruses with distinct genetic characteristics and geographical origins (clade A, B. C, D, E, F, G), viruses susceptible to antiretroviral drugs, viruses with reduced susceptibility/resistance to antiretroviral drugs, primary isolates, isolates adapted for growth in cell culture (often referred to as lab-adapted viruses), syncytia inducing (SI) viruses, non-syncytia inducing (NSI) viruses, macrophage (M) tropic viruses, T-cell (T) tropic viruses and dual tropic (M and T) viruses.

Characterization of Patient Antibody (Patient Antibody vs. Standard Virus Panel)

In this embodiment, the assay is performed using a target cell line that expresses the HIV-1 receptor CD4 plus the HIV-1 co-receptors CCR5 and CXCR4 (HT4/CCR5/CXCR4). Such a cell line is capable of evaluating the neutralizing activity of antibodies for both R5 and X4 tropic viruses. In a related embodiment, the assay is performed using two target cell lines. One cell line expresses CD4 plus CCR5 (U-87/CD4/CCR5) and is used to test R5 tropic viruses. Another cell line expresses CD4 plus CXCR4 (U-87/CD4/CXCR4) and is used to evaluate X4 tropic viruses. The virus entry assay is performed by infecting individual target cell cultures with recombinant virus stocks derived from packaging host cells transfected with pHIVenv and pHIVluc or pHIVlucDU3 vectors. In this embodiment, pHIVenv vectors contain envelope sequences of specific, well-characterized viruses and express the HIV-1 envelope proteins (gp120SU, gp41TM). Such viruses represent a "standard virus panel" (see above description of virus population). Some, but not all, reasonable examples of viruses that may constitute a standard panel are listed in Table 4. A standard virus panel is used to compare the neutralizing antibody activity of sera obtained from many different patients and/or animals (see above description of patient population). In this embodiment viruses are evaluated using target cells cultured in 96 well plates. Typically, target cells are plated at 5,000 cells per well for HT4/CCR5/CXCR4 or 10,000 cells per well for U-87/CD4/CCR5 and U-87/CD4/CXCR4 one day prior to infection. Prior to target cell infection, each virus stock is pre-incubated with the sera or antibody preparation (typically for 1 h) that is being evaluated. The sera or antibody preparations are tested undiluted and at incrementally greater dilutions (typically four to five serial 10-fold dilutions). Infection of target cells with each virus stock is also performed in the absence of antibody (no antibody). Virus neutralization is assessed by comparing the amount of luciferase activity produced in target cells, both in the presence and absence of antibody. In this embodiment, the results of the assay are interpreted by comparing the ability of each antibody to preferentially block infection of target cells (reduce or eliminate luciferase activity). Virus neutralization activity is quantified by noting the highest antibody dilution (most dilute) that is able to block target cell infection (e.g. the highest dilution that is able to reduce the luciferase activity produced in the absence of antibody by 50%).

Characterization of Patient HIV-1 (Patient Virus vs. Standard Antibody Panel)

In this embodiment, the assay is performed using a target cell line that expresses the HIV-1 receptor CD4 plus the HIV-1 co-receptors CCR5 and CXCR4 (HT4/CCR5/CXCR4). Such a cell line is capable of evaluating the neutralizing activity of antibodies for both R5 and X4 tropic viruses. In a related embodiment, the assay is performed using two target cell lines. One cell line expresses CD4 plus CCR5 (U-87/CD4/CCR5) and is used to test R5 tropic viruses. Another cell line expresses CD4 plus CXCR4 (U-87/CD4/CXCR4) and is used to evaluate X4 tropic viruses. The virus entry assay is performed by infecting individual target cell cultures with recombinant virus stocks derived from packaging host cells transfected with pHIVenv and pHIVluc or pHIVlucDU3 vectors. In this embodiment, pHIVenv vectors contain patient virus derived envelope sequences and express HIV-1 envelope proteins (gp120SU, gp41TM). In this embodiment, viruses from different patient populations (see above description of patient population), and/or different virus populations (see above description for virus population) are used to construct pHIVenv vectors. Pseudotyped HIV derived from pHIVenv vectors are evaluated in the virus entry assay to determine if they are susceptible to neutralization by a panel of specific, well-characterized antibody preparations. Such antibodies represent a "standard antibody panel". Some, but not all, reasonable examples of antibodies that may constitute a standard panel are listed in Table 4. In this embodiment virus neutralization is evaluated using target cells cultured in 96 well plates. Typically, target cells are plated at 5,000 cells per well for HT4/CCR5/CXCR4 or 10,000 cells per well for U-87/CD4/CCR5 and U-87/CD4/CXCR4 one day prior to infection. Prior to infection, each patient derived virus stock is incubated with the each of the antibody preparations (typically for 1 h) in the standard antibody panel. The sera or antibody preparations are tested undiluted and at various dilutions (typically four to five serial 10-fold dilutions). Infection of target cells with each virus stock is also performed in the absence of drug (no drug). Virus neutralization is assessed by comparing the amount of luciferase activity produced in target cells, both in the presence and absence of antibody. In this embodiment, the results of the assay are interpreted by comparing the ability of each antibody to preferentially block infection of target cells (reduce or eliminate luciferase activity). Virus neutralization activity is quantified by noting the highest antibody dilution (most dilute) that is able to block target cell infection (e.g. the highest dilution that is able to reduce the luciferase activity produced in the absence of antibody by 50%).

EXAMPLE 7

Identifying HIV-1 Envelope Amino Acid Sequences that Elicit Alter, or Prevent Neutralizing Antibody Responses This example provides a means and method for identifying HIV-1 envelope amino acid sequences that elicit/promote, or alter, or prevent antibody mediated neutralization of HIV-1 infection (also referred to as virus neutralization in this application).

Envelope sequences derived from patient samples, or individual clones derived from patient samples, or envelope sequences engineered by site directed mutagenesis to contain specific mutations, are tested in the entry assay to determine co-receptor tropism as described in Example 6.

In one embodiment, antibody mediated neutralization is evaluated in longitudinal patient samples (viruses collected from the same patient at different time points) is evaluated. For example, virus neutralization is evaluated prior to vaccination, during a course of vaccination, and at incremental time points after the course of vaccination is completed. In one embodiment, virus neutralization is evaluated for preventative vaccines. In another embodiment, virus neutralization is evaluated for therapeutic vaccines.

In another embodiment, virus neutralization is evaluated for samples collected from a large number of different patients. In a further embodiment, virus neutralization is evaluated for samples collected from a large number of patients representing different virus and patient populations. Such patient populations may include, but are not limited to, newly infected patients, chronically infected patients, patients with advanced disease, patients undergoing antiretroviral therapy or immuno-therapy, vaccinated and unvaccinated individuals. Such virus populations may include, but are not limited to, viruses with distinct genetic characteristics (clade A, B, C, D, E, F, G), viruses susceptible to antiretroviral drugs, viruses with reduced susceptibility/resistance to antiretroviral drugs, primary isolates or isolates adapted for growth in cell culture (often referred to as lab-adapted viruses), syncytia inducing (SI) viruses or non-syncytia inducing (NSI) viruses, macrophage (M) tropic viruses, T-cell (T) tropic viruses and dual tropic (M and T) viruses.

Genotypic Analysis of Patient HIV Samples

Envelope sequences representing patient sample pools, or clones derived from patient pools, can be analyzed by any broadly available DNA sequencing methods. In one embodiment of the invention, patient HIV sample sequences are determined using viral RNA purification, RT/PCR and dideoxynucleotide chain terminator sequencing chemistry and capillary gel electrophoresis (Applied Biosystems, Foster City, Calif.). Envelope sequences of patient virus pools or clones are compared to reference sequences, other patient samples, or to a sample obtained from the same patient prior to initiation of therapy, if available. The genotype is examined for sequences that are different from the reference or pre-treatment sequence and correlated to differences in entry inhibitor susceptibility.

Antibody Mediated Neutralization of Genetically Characterized Viruses

Envelope amino acid sequences that correlate with virus neutralization are evaluated by constructing envelope expression vectors (pHIVenv) containing a specific mutation on a defined genetic background (e.g. NL4-3 for X4 tropism, JRCSF for R5 tropism). Mutations may be incorporated alone and/or in combination with other mutations that are thought to modulate virus neutralization. Envelope mutations are introduced into pHIVenv vectors using any of the broadly available methods for site-directed mutagenesis. In one embodiment of this invention the mega-primer PCR method for site-directed mutagenesis is used (Sarkar, G. and Summer, S. S., 1990). A pHIVenv vector containing a specific envelope mutation or group of mutations are tested using the virus entry assay described in Example 6. Specific antibody preparations (i.e. well-characterized monoclonal of polyclonal antibody preparations), serum from HIV infected patients, or serum from vaccinated individuals can be selected to compare neutralizing activity. Antibody neutralization of the virus containing envelope mutations is compared to antibody neutralization of a genetically defined virus that lacks the specific mutations under evaluation. The ability of a specific mutation to confer, alter, or prevent antibody neutralization is confirmed or disproved by introducing the mutation into well-characterized reference virus and evaluating the antibody mediated neutralization of the mutant virus in the virus entry assay as described in Example 6. Observed changes in virus neutralization are attributed to the specific mutations introduced into the pHIVenv vector.

In one embodiment of the invention, genetic determinants of virus neutralization are identified by evaluating amino acid sequences within the V3 loop of the gp120 surface envelope protein. The amino acid sequences under evaluation are identified by comparing the amino acid sequences of large numbers of viruses that can, or cannot be neutralized by various well-characterized antibody preparations, patient sera, or sera from vaccinated individuals. Consistent differences in V3 loop amino acid sequences between viruses that can, or cannot be neutralized are selected for evaluation. Isogenic viruses based on an well-characterized parental clone (e.g NL4-3, HXB2, JRCSF) containing specific "virus neutralization candidate" mutations in the V3 loop of the gp120 envelope protein are constructed by site directed mutagenesis and tested for antibody mediated neutralization as described in Example 6. Cells expressing CD4 plus CCR5 (e.g. U-87/CD4/CCR5), CD4 plus CXCR4 (U-87/CD4/CXCR4), or CD4 plus CCR5 and CXCR4 (HT4/CCR5/CXCR4) are infected. Amino acid substitutions that change that elicit, alter, or prevent antibody neutralization are deemed important to virus neutralization.

In a related embodiment of the invention, genetic determinants of virus neutralization are identified by evaluating amino acid sequences within the entire gp120 surface envelope protein.

In a related embodiment of the invention, genetic determinants of virus neutralization are identified by evaluating amino acid sequences within the gp41 transmembrane envelope protein.

EXAMPLE 8

Measuring Susceptibility to Virus Entry Inhibitors to Guide Treatment Decisions

This example provides a means and method for using virus entry inhibitor susceptibility to guide the treatment of HIV-1. This example further provides a means and method for using virus entry inhibitor susceptibility to guide the treatment of patients that have received previous antiretroviral treatment with a virus entry inhibitor. This invention further provides the means and methods for using virus entry inhibitor susceptibility to guide the treatment of patients that have not received previous treatment with a virus entry inhibitor.

In one embodiment, the susceptibility of patient's viruses to virus entry inhibitors is used to guide the treatment of patients failing antiretroviral regimens that include one or more virus entry inhibitors. Treatment failure (also referred to as virologic failure) is generally defined as partially suppressive antiviral treatment resulting in detectable levels of virus, which is typically measured in the patient plasma). Guidance may include, but is not limited to, (a) clarification of available drug treatment options, (b) selection of more active treatment regimens, (c) clarification of the etiology of rising viral load in treated patients (i.e. poor adherence, drug resistance), and (d) reduction in the use of inactive and potentially toxic drugs. In this embodiment, resistance test vectors are derived from a patient virus samples and tested for susceptibility to various virus entry inhibitors using the phenotypic virus entry assay. Virus entry inhibitors may include, but are not limited to, fusion inhibitors (e.g. T-20, T-1249), co-receptors antagonists (AMD3100, AMD8664, TAK779, PRO542, and peperidin-1yl butane compounds) and CD4 antagonists (MAb 5A8). Appropriate treatment decisions are based on the results of the virus entry assay (e.g. see FIG. 4B) and additional relevant laboratory test results and clinical information.

In another embodiment, the susceptibility of patient's viruses to virus entry inhibitors is used to guide the treatment of patients that have not been previously treated with antiretroviral regimens that include one or more virus entry inhibitors. Guidance may include, but is not limited to, (a) clarification of available drug treatment options, (b) selection of more active treatment regimens, (c) clarification of the baseline susceptibility to virus entry inhibitors, and (d) reduction in the use of inactive and potentially toxic drugs. Determining baseline susceptibility of virus entry inhibitors in treatment naive patients is important for two reasons. First, the natural susceptibility of viruses to entry inhibitors can vary widely (e.g. see FIG. 4A). Second, the increased use of virus entry inhibitors will undoubtedly result in the generation of drug resistant variants that can be transmitted to newly infected individuals. In this embodiment, resistance test vectors are derived from a patient virus samples and tested for susceptibility to various virus entry inhibitors using the phenotypic virus entry assay. Virus entry inhibitors may include, but are not limited to, fusion inhibitors (e.g. T-20, T-1249), co-receptors antagonists (AMD3100, AMD8664, TAK779, PRO542, and peperidin-1yl butane compounds) and CD4 antagonists (MAb 5A8). Appropriate treatment decisions are based on the results of the virus entry assay and additional relevant laboratory test results and clinical information.

EXAMPLE 9

Measuring HIV-1 Co-receptor Tropism to Guide Treatment Decisions

This example provides a means and method for using HIV-1 co-receptor (CCR5, CXCR4) tropism to guide the treatment of HIV-1. This example further provides a means and method for using HIV-1 co-receptor tropism to guide the treatment of patients failing antiretroviral drug treatment. This invention further provides the means and methods for using HIV-1 co-receptor tropism to guide the treatment of patients newly infected with HIV-1.

This example provides a means and method for using virus HIV-1 co-receptor tropism to guide the treatment of HIV-1. This example further provides a means and method for using HIV-1 co-receptor tropism to guide the treatment of patients that have received previous antiretroviral treatment with a virus entry inhibitor. This invention further provides the means and methods for using HIV-1 co-receptor tropism to guide the treatment of patients that have not received previous treatment with a virus entry inhibitor.

In one embodiment, the co-receptor tropism of a patient's virus is used to guide the treatment of a patient failing antiretroviral regimens that include one or more co-receptor antagonists. Treatment failure (also referred to as virologic failure) is generally defined as partially suppressive antiviral treatment resulting in detectable levels of virus, which is typically measured in the patient plasma). Guidance may include, but is not limited to, (a) clarification of the etiology of rising viral load in treated patients (i.e. poor adherence, drug resistance, change in co-receptor tropism), (b) clarification of available drug treatment options, (c) selection of more active treatment regimens, and (d) reduction in the use of inactive and potentially toxic drugs. Monitoring co-receptor tropism in patients receiving treatment with CCR5 antagonists has clinical significance, since drug pressure may result in a switch to CXCR4 co-receptor tropism. X4 viruses (CXCR4 co-receptor tropism) are associated with a poorer prognosis compared to R5 viruses (CCR5 co-receptor tropism). In this embodiment, resistance test vectors are derived from a patient virus samples and tested for susceptibility to various co-receptor antagonists using the phenotypic virus entry assay. Co-receptor antagonists may include, but are not limited to, AMD3100, AMD8664, TAK779, PRO542, and peperidin-1yl butane compounds. Appropriate treatment decisions are based on the results of the virus entry assay (e.g. see FIG. 4B) and additional relevant laboratory test results and clinical information.

In another embodiment, co-receptor tropism of a patient's virus is used to guide the treatment of patients that have not been previously treated with antiretroviral regimens that include one or more co-receptor antagonists. Guidance may include, but is not limited to, (a) clarification of the baseline co-receptor tropism, (b) clarification of available drug treatment options, (c) selection of more active treatment regimens, (d) reduction in the use of inactive and potentially toxic drugs. Determining baseline co-receptor tropism has significant clinical significance. Treatment with the appropriate co-receptor antagonist (R5 vs. X4 tropism), or antagonists (dual tropism or mixed tropism) is likely to result in a more potent and durable response. In this embodiment, resistance test vectors are derived from a patient virus samples and tested for susceptibility to various virus entry inhibitors using the phenotypic virus entry assay. Co-receptors antagonists may include, but are not limited to, AMD3100, AMD8664, TAK779, PRO542, and peperidin-1yl butane compounds. Appropriate treatment decisions are based on the results of the virus entry assay and additional relevant laboratory test results and clinical information.

REFERENCES

1. Adachi, A., H. E. Gendelman, S. Koenig, T. Folks, R. Caney, A. Rabson, and M. A. Martin. 1986. Production of Acquired Immunodeficiency Syndrome-associated Retrovirus in Human and Nonhuman Cells Transfected with an Infectious Molecular Clone. *J. Virol.* 59:284–291.
2. Alkhatib, G., C. Combadiere, C. C. Broder, Y. Feng, P. E. Kennedy, P. M. Murphy, and E. A. Berger. 1996. CC CKR5: A Rantes, MIP-1alpha, MIP-1 Beta Receptor as a Fusion Cofactor for Macrophage-tropic Hiv-1. *Science* 272:1955–8.

3. Allaway G. P., Ryder A. M., Beaudry G. A., and Maddon P. J. 1993. Synergistic Inhibition of HIV-1 Envelope-Mediated Cell Fusion by CD4-based Molecules in Combination with Antibodies to Gp120 or Gp41. *Aids Res. Hum. Retroviruses* 9:581–7.

4. Baba, M., O. Nishimura, N. Kanzaki, M. Okamoto, H. Sawada, Y. Iizawa, M. Shiraishi, Y. Aramaki, K. Okonogi, Y. Ogawa, K. Meguro, and M. Fujino. 1999. A Small-molecule, Nonpeptide CCR5 Antagonist with Highly Potent and Selective Anti-hiv-1 Activity. *Proc. Natl. Acad. Sci.* USA 96:5698–703.

5. Baxter, J., D. Mayers, D. Wentworth, J. Neaton, and T. Merigan. 1999. A Pilot Study of the Short-term Effects of Antiretroviral Management Based on Plasma Genotypic Antiretroviral Resistance Testing (Gart) in Patients Failing Antiretroviral Therapy. *Presented at the 6th Conference on Retroviruses and Opportunistic Infections*. Chicago, Ill.

6. Bernard P., Kezdy K. e., Van Melderen L., Steyaerz J., Wyns L., Pato M. l., Higgins P. N., and Couturier M. 1993. The F Plasmid CcdB protein Induces Efficient ATP-dependent Dna Cleavage by Gyrase. *J. Mol. Biol.* 23:534–41.

7. Bernard, P. and Couturier, M. 1992. Cell Killing by the F Plasmid Ccdb protein Involves Poisoning of DNA-topoisomerase II Complexes. *J. Mol. Bio.* 226:735–45.

8. Bleul, C. C., M. Farzan, H. Choe, C. Parolin, I. Clark-Lewis, J. Sodroski, and T. A. Springer. 1996. The Lymphocyte Chemoattractant Sdf-1 Is a Ligand for Lestr/fusin and Blocks Hiv-1 Entry. *Nature* 382:829–33.

9. Bridger G. J, Skerlj R. T., Padmanabhan S., Martellucci S. A., Henson G. W., Struyf S., Witvrouw M., Schols D., and De Clercq E. 1999. Synthesis and Structure-activity Relationships of Phenylenebis (methylene)-linked Bis-azamacrocycles That Inhibit HIV-1 and HIV-2 Replication by Antagonism of the Chemokine Receptor CXCR4. *J. Med. Chem.* 42:3971–81.

10. Carpenter, C. J., Cooper D. A., Fischl, M. A., Gatell J. M., Gazzard B. G., Hammer S. M., Hirsch M. s., Jacobsen D. M., Katzenstein D. A., Montaner J. S., Richman D., Saag M. S., Schechter M., Schooley R. T., Thompson M. A., Vello S., Yeni P. G., and Volberding P. A. 2000. Antiretroviral Therapy in Adults. *JAMA* 283:381–89.

11. CDC (Centers for Disease Control and Prevention). HIV/AIDS Surveillance Report, 1999;11 (no. 1).

12. Coffin, J. m. 1995. HIV Population Dynamics in Vivo: Implications for Genetic Variation, Pathogenesis, and Therapy. *Science* 267:483–489.

13. DHHS (Department of Health and Human Services). Henry Kaiser Family Foundation: Guidelines for the Use of Antiretrovirals Agents in HIV-infected Adults and Adolescents. (Jan. 28, 2000).

14. Gerdes, K., L. k. Poulsen, T. Thisted, A. k. Nielson, J. MaRTInussen, and P. h. Andreasen. 1990, The Hok Killer Gene Family in Gram-negative Bacteria. *The New Biologist:* 2:946–956.

15. Hertogs, K., M.-p. De Béthune, V. Miller, T. Ivens, P. Schel, A. V. Cauwenberge, C. Van Den Eynde, V. Van Gerwen, H. Azijn, M. Van Houtte, F. Peeters, S. Staszewski, M. Conant, S. Bloor, S. Kemp, B. Larder, and R. Pauwels. 1998. A Rapid Method for Simultaneous Detection of Phenotypic Resistance to Inhibitors of protease and Reverse Transcriptase in Recombinant Human Immunodeficiency Virus Type 1 Isolates from Patients Treated with Antiretroviral Drugs. *Antimicrob. Agents Chemother.* 42:269–276.

16. Hwang, J.-j., L. Li, W. f. Anderson. 1997. A Conditional Self-inactivating Retrovirus Vector That Uses a Tetracycline-responsive Expression System. *J. Virol.* 71: 7128–7131.

17. Japour, A. J., D. L. Mayers, V. A. Johnson, D. R. Kuritzkes, L. A. Beckett, J.-m. Arduino, J. Lane, B. R. j., P. S. Reichelderfer, R. T. D-aquila, C. S. Crumpacker, T. R.-s. Group, T. A. C. T. Group, and V. C. R. W. Group. 1993. Standardized Peripheral Blood Mononuclear Cell Culture Assay for Determination of Drug Susceptibilities of Clinical Human Immunodeficiency Virus Type 1 Isolates. Antimicrob. Agents Chemother. 37:1095–1101.

18. Judice J. k., Tom J. y., Huang W., Wrin T., Vennari J., Petropoulos C. j., and Mcdowell R. s. 1997. Inhibition of HIV Type 1 Infectivity by Constrained Alpha-helical Peptides: Implications for the Viral Fusion Mechanism. *proc. Natl. Acad. Sci. U S a* 94:13426–30.

19. Kilby Jm, Hopkins S, Venetta Tm, Dimassimo B, Cloud Ga, Lee Jy, Alldredge L, Hunter E, Lambert D, Bolognesi D, Matthews T, Johnson Mr, Nowak Ma, Shaw Gm, and Saag Ms. 1998. Potent Suppression of Hiv-1 Replication in Humans by T-20, a Peptide Inhibitor of Gp41-mediated Virus Entry. *Nat Med* 4:1302–7.

20. Mascola, J. r., G. Stiegler, T. c. Vancott, H. Katinger, C. b. Carpenter, C. e. Hanson, H. Beary, D. Hayes, S. s. Frankel, D. l. Birx, and M. g. Lewis. 2000. protection of Macaques Against Vaginal Transmission of a Pathogenic Hiv-1/siv Chimeric Virus by Passive Infusion of Neutralizing Antibodies. Nature Med. 6:207–210.

21. Miyoshi, H., B. Ulrike, M. Takahashi, F. h. Gage, and I. m. Verma. 1998. Development of a Self-inactivating Lentivirus Vector. J. Virol. 72:8150–5157.

22. Naviaux, R. k., E. Costanzi, M. Haas, and I. m. Verma. 1996. The Pcl Vector System: Rapid production of Helper-free, High-titer, Recombinant Retroviruses. J. Virol. 70: 5701–5705.

23. Petropoulos, C. j., N. t. Parkin, K. l. Limoli, Y. s. Lie, T. Wrin, W. Huang, H. Tian, D. Smith, G. a. Winslow, D. Capon and J. m. Whitcomb. 2000. A Novel Phenotypic Drug Susceptibility Assay for Hiv-1. Antimicrob. Agents & Chem. 44:920–928.

24. Phrma (Pharmaceutical Research and Manufacturers of America). New Medicines in Development for Aids 1999. Htt://www.phrma.org.

25. Piketty, C., E. Race, P. Castiel, L. Belec, G. Peytavin, A. Si-mohamed, G. Gonzalez-canali, L. Weiss, F. Clavel, and M. Kazatchkine. 1999. Efficacy of a Five-drug Combination Including Ritonavir, Saquinavir and Efavirenz in Patients Who Failed on a Conventional Triple-drug Regimen: Phenotypic Resistance to protease Inhibitors predicts Outcome of Therapy. Aids: 13:f71–f77.

26. Porter, C. c., K. v. Lukacs, G. Box, Y. Takeuchi, and M .k. l. Collins. 1998. Cationic Liposomes Enhance the Rate of Transduction by a Recombinant Retroviral Vector in Vitro and in Vivo. J. Virol. 72:4832–4840.

27. Reimann K. a., Cate R. l., Wu Y., Palmer L., Olson D., Waite B. c., Letvin N. l., and Burkly L. c. 1995. In Vivo Administration of CD4-specific Monoclonal Antibody: Effect on provirus Load in Rhesus Monkeys Chronically Infected with the Simian Immunodeficiency Virus of Macaques. *Aids Res. Hum. Retroviruses* 11:517–25

28. Retroviruses. Coffin, J., S. Hughes, H. Varmus (Eds). 1997. Cold Spring Harbor Laboratory press, Cold Spring Harbor, N.Y.

29. Richman, D. 1998. Nailing down Another HIV Target. Nature Med. 4:1232–1233.
30. Rimsky, L. T., D. C. Shugars, and T. J. Matthews. 1998. Determinants of Human Immunodeficiency Virus Type 1 Resistance to Gp41-derived Inhibitory Pepitides. J. Virol. 72:986–993.
31. Rodriguez-rosado, R., Briones, C. and Soriano, V. 1999. Introduction of HIV Drug-resistance Testing in Clinical practice. Aids 13:1007–1014.
32. Schinazi, R. f, Larder, B. a., and Mellors, J. w. 1999. Mutations in Retroviral Genes Associated with Drug Resistance. Intl. Antiviral News: 7:46–69
33. Shi C., and J. w. Mellors. 1997. A Recombinant Retroviral System for Rapid in Vivo Analysis of Human Immunodeficiency Virus Type 1 Susceptibility to Reverse Transcriptase Inhibitors. Antimicrob. Agents Chemother 41:2781–2785.
34. Stephenson, J. 1999. New Class of Anti-hiv Drugs. Jama 282:1994.
35. Who, Unaids/world Health Organization. Report: Aids Epidemic Update: December 1999. Http://www.unaids.org/publications/documents/epidemiology.
36. Wild, C., T. Oak, C. Mcdanal, D. Bolognesi, and T. Matthews. 1992. A Synthetic Peptide Inhibitor of HIV Replication: Correlation Between Solution Structure and Viral Inhibition. *Proc. Natl. Acad. Sci.* USA 89:10537–10541.
37. Zennou, V., F. Mammamo, S. Paulous, D. Mathez, and F. Clavel. 1998. Loss of Viral Fitness Associated with Multiple Gag and Gag-pol processing Defects in Human Immunodeficiency Virus Type 1 Variants Selected for Resistance to protease Inhibitors in Vivo. *J. Virol:* 72:3300–06.
38. Ziermann, R., K. Limoli, K. Das, E. Arnold, C. j. Petropoulos, and N. t. Parkin. 2000. A Mutation in Hiv-1 protease, N88s, That Causes in Vitro Hypersensitivity to Amprenavir. *J. Virol.* 74:4414–4419.

What is claimed is:

1. A method for identifying whether a compound inhibits cellular entry of a population of virus infecting a patient, comprising:
   (a) contacting a population of virus with cells in the presence of the compound, wherein the cells express a cell surface receptor and/or co-receptor to which the population of virus binds, and wherein the population of virus comprise: (i) a viral expression vector that lacks a nucleic acid encoding a viral envelope protein and which comprises an indicator nucleic acid that produces a detectable signal, and (ii) a population of envelope proteins derived from the population of virus infecting the patient;
   (b) measuring the amount of detectable signal produced by the cells;
   (c) contacting the population of virus of step (a) with a second sample of cells, wherein the second sample of cells express a cell surface receptor and/or co-receptor which binds to the virus;
   (d) measuring the amount of detectable signal produced by the second sample of cells in step (c) in order to determine the infectivity of the population of virus; and
   (e) comparing the amount of signal measured in step (b) with the amount of signal measured in step (d), wherein a decrease in the amount of detectable signal indicates the compound inhibits cellular entry of the population of virus infecting the patient.

2. The method of claim 1, wherein the population of envelope proteins is produced by co-transfecting into a cell (i) a population of envelope nucleic acids obtained from the population of virus infecting the patient, wherein the population of envelope nucleic acids encodes the patient population of envelope proteins and (ii) a viral expression vector lacking a nucleic acid encoding an envelope protein, wherein the vector comprises an indicator nucleic acid that produces a detectable signal.

3. The method of claim 1, wherein steps (a) and (b) are repeated with varying concentrations of compounds and the amounts of signal generated for each of the concentrations are compared in step (c).

4. The method of claim 3, further comprising generating a plot of viral infectivity based on compound concentrations.

5. The method of claim 4, further comprising generating an IC50 from the plot.

6. The method of claim 1, wherein the indicator nucleic acid comprises an indicator gene.

7. The method of claim 6, wherein the indicator gene is a luciferase gene.

8. The method of claim 1, wherein the virus is HIV-1.

9. The method of claim 1, wherein the receptor is CD4.

10. The method of claim 1, wherein the co-receptor is CXCR4 or CCR5.

11. The method of claim 10, wherein the co-receptor is CXCR4.

12. The method of claim 10, wherein the co-receptor is CCR5.

13. The method of claim 2, wherein the envelope nucleic acids comprise nucleic acids that encode the envelope polyprotein (gp160).

14. The method of claim 2, wherein the envelope nucleic acids comprise nucleic acids that encode the surface envelope protein (gp120) and the transmembrane envelope protein (gp41).

15. The method of claim 1, wherein the viral expression vectors comprise an HIV nucleic acid.

16. The method of claim 1, wherein the viral expression vectors comprise an HIV gag-pol gene.

17. The method of claim 2, wherein the cells are mammalian.

18. The method of claim 17, wherein the mammalian cells are human.

19. The method of claim 18, wherein the human cells are human embryonic kidney cells.

20. The method of claim 19, wherein the human embryonic kidney cells are 293 cells.

21. The method of claim 18, wherein the human cells are human T cells.

22. The method of claim 18, wherein the human cells are peripheral blood mononuclear cells.

23. The method of claim 1, wherein the cells are astroglioma cells.

24. The method of claim 23, wherein the astroglioma cells are U87 cells.

25. The method of claim 1, wherein the cells are human osteosarcoma cells.

26. The method of claim 25, wherein the osteosarcoma cells are HT4 cells.

27. The method of claim 1, wherein the compound binds to the receptor or co-receptor.

28. The method of claim 27, wherein the compounds binds the receptor CD4.

29. The method of claim 27, wherein the compound binds the co-receptor CXCR4 or CCR5.

30. The method of claim 29, wherein the compound binds the co-receptor CXCR4.

31. The method of claim 29, wherein the compounds binds the co-receptor CCR5.

32. The method of claim 1, wherein the compound comprises an antibody.

33. The method of claim 1, wherein the compound is a ligand of the cell surface receptor.

34. The method of claim 1, wherein the compound inhibits membrane fusion.

35. The method of claim 1, wherein the compound is a peptide, a peptidomimetic, an organic molecule, or a synthetic compound.

36. The method of claim 1, wherein the compound binds the viral envelope.

* * * * *

SEQUENCE LISTING

<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: RT Primers
    for HIV envelope

<400> SEQUENCE: 1
ggagcattta caagcagcaa cacagc                                          26

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: RT Primers
    for HIV envelope

<400> SEQUENCE: 2
ttccagtcav acctcaggta c                                               21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: RT Primers
    for HIV envelope

<400> SEQUENCE: 3
agaccaatga cttayaagg                                                  19

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: PCR primer

<400> SEQUENCE: 4
gggctcgaga ccggtcagtg gcaatgagag tgaag                                35

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: PCR primer

<400> SEQUENCE: 5
gggctcgaga ccggtgagca gaagacagtg gcaatga                    37

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: PCR primer

<400> SEQUENCE: 6
gggctcgaga ccggtgagca gaagacagtg gcaatg                     36

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: PCR primer

<400> SEQUENCE: 7
gggtctagaa cgcgttgcca cccatcttat agcaa                      35

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: PCR primer

<400> SEQUENCE: 8
gggtctagaa cgcgtccact tgccacccat bttatagc                   38

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 9
gggtctagaa cgcgtccact tgccacccat btta                       34

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: PCR primer

<400> SEQUENCE: 10
gatggtctaa gacgctgttc aatatccctg cctaactc                   38

<210> SEQ ID NO 11
<211> LENGTH: 10
<212> TYPE: PRT
<213> ORGANISM: Artificial Sequence
<220> FEATURE:

```
<223> OTHER INFORMATION: Description of Artificial Sequence: Viral Entry
      Inhibitor Resistance Mutation

<400> SEQUENCE: 11

Gln Leu Leu Ser Gly Ile Val Gln Gln Gln
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Viral Entry
      Inhibitor Resistance Mutation

<400> SEQUENCE: 12

Gln Leu Leu Ser Ser Ile Met Gln Gln Gln
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Viral Entry
      Inhibitor Resistance Mutation
<220> FEATURE:
<221> NAME/KEY: MISC_FEATURE
<222> LOCATION: (5)..(5)
<223> OTHER INFORMATION: Where X= G or S
<220> FEATURE:
<221> NAME/KEY: MISC_FEATURE
<222> LOCATION: (7)..(7)
<223> OTHER INFORMATION: Where X= V or M

<400> SEQUENCE: 13

Gln Leu Leu Ser Xaa Ile Xaa Gln Gln Gln
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Viral Entry
      Inhibitor Resistance Mutation

<400> SEQUENCE: 14

Gln Leu Leu Ser Asp Ile Val Gln Gln Gln
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Viral Entry
      Inhibitor Resistance Mutation
<220> FEATURE:
<221> NAME/KEY: MISC_FEATURE
<222> LOCATION: (5)..(5)
<223> OTHER INFORMATION: Where X= G or D

<400> SEQUENCE: 15

Gln Leu Leu Ser Xaa Ile Val Gln Gln Gln
1               5                   10

<210> SEQ ID NO 16
<211> LENGTH: 36
```

-continued

```
<212> TYPE: PRT
<213> ORGANISM: Artificial Sequence
<220> FEATURE:
<223> OTHER INFORMATION: Description of Artificial Sequence: Fusion
      Inhibitor Peptide

<400> SEQUENCE: 16

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
            35
```